United States Patent
Scheinberg et al.

(10) Patent No.: US 9,976,137 B2
(45) Date of Patent: May 22, 2018

(54) TARGETED SELF-ASSEMBLY OF FUNCTIONALIZED CARBON NANOTUBES ON TUMORS

(71) Applicants: David A. Scheinberg, New York, NY (US); Michael R. McDevitt, Bronx, NY (US); Carlos H. Villa, Philadelphia, PA (US); J. Justin Mulvey, New York, NY (US)

(72) Inventors: David A. Scheinberg, New York, NY (US); Michael R. McDevitt, Bronx, NY (US); Carlos H. Villa, Philadelphia, PA (US); J. Justin Mulvey, New York, NY (US)

( * ) Notice: Subject to any disclaimer, the term of this patent is extended or adjusted under 35 U.S.C. 154(b) by 568 days.

(21) Appl. No.: 14/318,112

(22) Filed: Jun. 27, 2014

(65) Prior Publication Data
US 2014/0308203 A1    Oct. 16, 2014

Related U.S. Application Data

(63) Continuation-in-part of application No. PCT/US2012/071915, filed on Dec. 28, 2012.

(60) Provisional application No. 61/581,228, filed on Dec. 29, 2011.

(51) Int. Cl.
| | |
|---|---|
| *A61K 51/00* | (2006.01) |
| *A61M 36/14* | (2006.01) |
| *C12N 15/113* | (2010.01) |
| *A61K 51/12* | (2006.01) |
| *A61K 51/10* | (2006.01) |
| *C12N 15/11* | (2006.01) |
| *C07K 16/28* | (2006.01) |
| *C07K 16/30* | (2006.01) |
| *A61K 47/68* | (2017.01) |
| *B82Y 5/00* | (2011.01) |

(52) U.S. Cl.
CPC ........ *C12N 15/113* (2013.01); *A61K 47/6849* (2017.08); *A61K 51/1027* (2013.01); *A61K 51/1093* (2013.01); *A61K 51/1203* (2013.01); *A61K 51/1248* (2013.01); *C07K 16/2803* (2013.01); *C07K 16/2887* (2013.01); *C07K 16/30* (2013.01); *C12N 15/111* (2013.01); *B82Y 5/00* (2013.01); *C07K 2317/92* (2013.01); *C12N 2310/113* (2013.01); *C12N 2310/3233* (2013.01); *C12N 2310/351* (2013.01); *C12N 2320/32* (2013.01); *Y10S 977/75* (2013.01); *Y10S 977/842* (2013.01); *Y10S 977/906* (2013.01)

(58) Field of Classification Search
CPC .... A61K 51/00; A61K 51/1093; A61K 47/00; A61K 47/48561; A61K 51/1203; A61K 51/1248; A61K 51/1027; A61K 38/00; A61K 51/088; A61K 51/0478; A61K 49/0004; A61K 49/0008; A61K 2123/00; A61K 2121/00; A61K 47/6849; C12N 15/113; C12N 15/111; C12N 2310/351; C12N 2310/3233; C12N 2310/113; C12N 2320/32; C07K 16/2887; C07K 16/2803; C07K 16/30; C07K 2317/92; Y10S 977/906; Y10S 977/842; Y10S 977/75; B82Y 5/00

USPC ............. 424/1.11, 1.49, 1.65, 1.73, 9.1, 9.2; 514/1, 1.1, 19.2, 19.3, 19.4, 19.5, 19.6; 977/742, 743, 744, 745, 750, 752, 754, 977/755, 773

See application file for complete search history.

(56) References Cited

U.S. PATENT DOCUMENTS

| | | | |
|---|---|---|---|
| 8,540,965 B2 * | 9/2013 | Scheinberg | A61K 47/48869 424/9.1 |
| 2011/0158913 A1 * | 6/2011 | Hnatowich | A61K 49/0032 424/9.6 |

OTHER PUBLICATIONS

Villa et al, Nano Lett., Dec. 2008, Vo. 8, No. 12, pp. 4221-4228.*

* cited by examiner

*Primary Examiner* — D L Jones
(74) *Attorney, Agent, or Firm* — Benjamin Aaron Adler

(57) ABSTRACT

Provided herein are methods for delivering a molecule in situ to a cell and for treating a cancer via the in situ delivery. The methods comprise contacting or administering to the cell, as two separate components, a morpholino oligonucleotide comprising a targeting moiety followed by a single wall nanotube construct comprising second morpholino oligonucleotides complementary to the first morpholino oligonucleotides and one or both of a therapeutic or diagnostic payload molecule linked to the single wall nanotube construct. Upon self-assembly of a single wall nanotube complex via hybridization of the first morpholino and second complementary morpholino oligonucleotides at the cell, the payload molecule is delivered. Also provided is the two component self-assembly single wall nanotube system and the single wall nanotube construct comprising the second component.

8 Claims, 15 Drawing Sheets

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: morpholino oligonucleotide sequence MORF
<220> FEATURE:
<221> NAME/KEY: misc_feature
<222> LOCATION: (1)..(18)
<223> OTHER INFORMATION: morpholine ring replaces deoxyribose for each
      nucleotide
<220> FEATURE:
<221> NAME/KEY: misc_feature
<222> LOCATION: (18)..(18)
<223> OTHER INFORMATION: 3' primary amine attached

<400> SEQUENCE: 1
tcttctactt cacaacta                                                 18

<210> SEQ ID NO 2
<211> LENGTH: 18
<212> TYPE: DNA
<213> ORGANISM: Artificial Sequence
<220> FEATURE:
<223> OTHER INFORMATION: complementary morpholino oligonucleotide
      sequence cMORF
<220> FEATURE:
<221> NAME/KEY: misc_feature
<222> LOCATION: (1)..(18)
<223> OTHER INFORMATION: morpholine ring replaces deoxyribose for each
      nucleotide
<220> FEATURE:
<221> NAME/KEY: misc_feature
<222> LOCATION: (18)..(18)
<223> OTHER INFORMATION: 3' primary amine attached

<400> SEQUENCE: 2
tagttgtgaa gtagaaga                                                 18
```

TARGETED SELF-ASSEMBLY OF FUNCTIONALIZED CARBON NANOTUBES ON TUMORS

CROSS-REFERENCE TO RELATED APPLICATIONS

This application is a continuation-in-part under 35 U.S.C. § 120 of international application PCT/US2012/071915, filed Dec. 28, 2012, which claims benefit of priority under 35 U.S.C. § 119(e) to provisional application U.S. Ser. No. 61/581,228, filed Dec. 29, 2011, the entirety of both of which are hereby incorporated by reference.

FEDERAL FUNDING LEGEND

This invention was made with government support under grants PO1 CA33049, RO1 CA55349, R21CA128406, and GM07739 awarded by the National Institutes of Health and grant DE-SC0002456 awarded by the U.S. Department of Energy. The government has certain rights in the invention.

BACKGROUND OF THE INVENTION

Field of the Invention

The present invention relates generally to the fields of nanomedicine, cancer treatment and tumor targeting. More specifically, the present invention relates to a self-assembly single wall nanotube complex functionalized to deliver a molecule to a cell, for example, a cancer cell, in situ.

Description of the Related Art

The rapidly expanding field of nanomedicine has begun to produce clinical successes in the first generation of engineered drug nanoparticles (1-2). Nanomedicine involves the use of synthetic nanoscale particles that aim to take advantage of the size, shape, and charge of materials to improve drug delivery or efficacy. In addition, the intrinsic properties of some nanomaterials result in unique physicochemical properties. Carbon nanotubes have seen widening application in biomedical research (3), in part because of the potential to append a diverse set of ligands, including small molecules (4), peptides (5-6), oligonucleotides (7), radioisotopes (8), monoclonal antibodies (9-10), and other targeting moieties.

The pharmacokinetics and pharmacodynamics of carbon nanotubes appear to depend highly on the chemical approaches used to render them water dispersable and biocompatible (11-12). Functionalization and dispersion imparts stability in aqueous environments and mitigates potential toxic effects (13). An important feature of covalently functionalized single-walled carbon nanotubes that allows their use as drug carriers is their rapid renal clearance via longitudinal renal glomerular filtration despite apparently large molecular weights (14-16). This clearance phenomenon has been termed fibrillar pharmacology and directly contrasts with the pharmacokinetic profiles of globular proteins.

Typically, in systemic targeting of malignancies, drug delivery vehicles such as mAb or nanoparticles are appended with cytotoxic effectors such as a chemotherapeutic small molecule or radioisotopes in a "single-step" process. However, prolonged half-lives of the effector molecules in vivo, especially those unbound or in excess, will increase toxicity. In contrast, a short circulation time of the agent is problematic as it reduces the time in which a high enough concentration can be maintained in the bloodstream to drive tumor penetration and cell binding.

Two step targeting or pre-targeting separates the required, slow, non-toxic tumor-targeting process of the vehicle from the necessary rapid clearance of the cytotoxic agent to achieve the desired pharmacokinetic goals (17). In this approach, a long-circulating tumor selective agent, such as a monoclonal antibody, is first administered and allowed a sufficient circulation time, typically 2-5 days, to accumulate at the tumor and clear the bloodstream. This is followed by a rapidly cleared, i.e., half life of <10 min, second-step agent, armed with the cytotoxic or diagnostic effector, that has a high-affinity interaction with the initial agent. This interaction may involve streptavidin-biotin (18), bispecific antibody-hapten (19), oligonculeotide hybridization (20), or, more recently, covalent 'click' chemistry (21). The second agent rapidly equilibrates with the initial agent, while also clearing the bloodstream. This approach allows for improved ratios of the cytotoxic or imaging agent in the tumor to that in the blood and the corresponding 'area under the curve' in concentration versus time, and in other off-site tissues. Pretargeting approaches have been previously explored (22-24), but did not include a second step reagent that both delivered a large payload and cleared quickly, enhancing the therapeutic index.

Because the second step in such a strategy requires rapid clearance, this agent is nearly always a small molecule such as a modified biotin, or a lone, short oligonucleotide. However, small molecules limit potency and sensitivity, as they are usually mono-substituted with the therapeutic or imaging agent, respectively. A highly multivalent effector as a second step should allow for amplification of signal, such as a toxin or diagnostic nuclide, multi-functionality, as well as improved binding affinity (25-26). However, such multivalent constructs as a second step are often too large to allow for the rapid clearance time necessary to avoid toxicity. Therefore, a covalently modified single-walled carbon nanotubes may offer the unique advantage of being highly multivalent and multi-functional while maintaining their rapid clearance.

Thus, there is a recognized need in the art for improved methods for multi-step delivery of a diagnostic and/or a therapeutic molecule or compound using single wall nanotube constructs. The prior art is deficient in the lack of self-assembly single wall nanotube systems effective to deliver a diagnostic and/or therapeutic compound via a two step-cell targeting method without prolonged exposure to a cytotoxic agent during targeting of the cell. The present invention fulfills this longstanding need and desire in the art.

SUMMARY OF THE INVENTION

The present invention is directed to a method of delivering a molecule in situ to a cell of interest. The method comprises contacting the cell with a first component comprising a morpholino oligonucleotide linked to a targeting moiety selective for the cell and contacting the morpholino oligonucleotide linked to the cell of interest via the targeting moiety with a second component comprising a soluble single wall nanotube construct having a plurality of morpholino oligonucleotides complementary to the targeting moiety-linked morpholino oligonucleotide and a plurality of the molecules independently linked to the SWNT such that the molecules comprise a deliverable payload. The morpholino oligonucleotide hybridizes to the complementary morpholino oligonucleotide to form a self-assembled soluble soluble single wall nanotube complex at the cell, wherein after hybridization the payload molecules are delivered in situ to the cell.

The present invention also is directed to a related method for diagnosing a cancer in a subject. In the method the cell of interest is a cell associated with cancer in a subject and the deliverable payload comprises molecules diagnostic of the cancer. The method further comprises comprising detecting the diagnostic payload molecules after in situ delivery thereof to the cancer-associated cell in the subject, thereby diagnosing the cancer.

The present invention also is directed to another related method for treating a cancer in a subject. In the method the cell of interest is a cell associated with cancer in a subject and the deliverable payload comprises molecules therapeutic against the cancer. The method further comprises treating the cancer with the therapeutic molecules after in situ delivery thereof to the cancer-associated cell in the subject.

The present invention is directed further to a self-assembly single walled nanotube (SWNT) system. The self-assembly SWNT system is a two-component system. The first component has a morpholino oligonucleotide linked to a monoclonal antibody. The second component has a plurality of complementary morpholino oligonucleotides and a plurality of one or both of a diagnostic or therapeutic molecules each independently linked to the SWNT.

The present invention is directed further still to a single wall nanotube construct. The single wall nanotube construct comprises a plurality of a bifunctional chelator covalently linked to the single wall nanotube, a radionuclide chelated to each bifunctional chelator and a plurality of morpholino oligonucleotides conjugated to the single wall nanotube.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 1A-1B show a synthetic scheme for chemical functionalization of SWNT-NH$_2$ to produce radio- and fluorescent labeled SWNT-cMORF conjugates. FIG. 1C is a 3D gel permeation HPLC chromatograph of compound 3 (SWNT-cMORF-NH$_2$) tracing the spectrum of eluted material across time. Only a single peak is evident and the spectrum is consistent with single-walled carbon nanotubes modified with bis-aryl hydrazone groups (shoulder at λ=~354 nm) and decreasing absorption through 600 nm, which is a quality of all nanotubes. FIG. 1D is a diagrammatic representation (not to scale) of SWNT-cMORF self-assembly onto mAb-MORF targeted tumor cells. The triangle is tumor antigen; the dot is appended cytotoxic or diagnostic moiety.

FIG. 2A shows a size exclusion HPLC of SWNT-cMORF alone (right peak), anti-CD20-MORF alone (middle peak), and SWNT-cMORF mixed with anti-CD20-MORF (left peak). FIG. 2B that a similar result is obtained when combining the SWNT-cMORF-$^{111}$In(DOTA) with anti-CD20-MORF and tracking the radiolabel associated with the either the SWNT-cMORF alone (solid line) or when mixed with the antibody (dashed line). FIG. 2C shows similar peak shift patterns are seen with SWNT-cMORF-$^{111}$In(DOTA) mixed with anti-A33-MORF antibodies, demonstrating that the complex formation is independent of antibody identity. FIG. 2D shows that the complex formation still occurred when the two components were mixed in the presence of 100% serum (dashed line) and this could be blocked when excess free cMORF was added to the mixture (solid line). FIG. 2E shows that SWNT-cMORF-$^{111}$In(DOTA) could be captured by protein A beads only when a complementary mAb-MORF was added.

FIG. 3A shows quantitation of flow cytometric assay of binding of SWNT-cMORF-AF647 onto HL60 cells. Pretreatment was with HL60 specific anti-CD33-MORF, isotype control anti-CD20-MORF, or specific anti-CD33-MORF+blocking with excess free cMORF. Data is presented as the change in median fluorescence. FIG. 3B shows quantitation of flow cytometric assay of binding of SWNT-cMORF-AF647 onto DAUDI cells. Pretreatment was with DAUDI specific anti-CD20-MORF, isotype control anti-CD33-MORF, or specific anti-CD20-MORF+blocking with excess free cMORF. FIG. 3C shows quantitation of flow cytometric assay of binding of SWNT-cMORF-AF647 onto LS174T cells. Pretreatment was with LS174T specific anti-A33-MORF, isotype control anti-CD33-MORF, or specific anti-A33-MORF+blocking with excess free cMORF. FIG. 3D shows a representative flow cytometric histogram of cell binding assay with SWNT-cMORF-AF647 on untreated (red), isotype control pretargeted (black), specific pretargeted+cMORF block (blue), or specific pretargeted (green) cells. FIG. 3E shows a binding curve for SWNT-cMORF-AF647 onto anti-CD20 pretargeted Daudi cells (squares) and anti-A33 pretargeted LS174T cells (triangles). Curves were fit using GraphPad Prism using an algorithm for one-site specific binding with variable Hill slope ($R^2$=0.95, 0.97).

FIG. 4A shows that anti-A33 (row 2) remained stably bound to LS174T cells (row 1, DAPI nuclear stain) at 37 8 C for up to 24 h (4 h is shown) and were evenly distributed about the cell membrane. FIG. 4B shows that anti-A33-MORF conjugates (rows 2 and 5) exhibited similar surface stability when bound to LS174T cells (blue, rows 1 and 3). High-power images are provided (rows 4, 5 and 6), as well 647 nm views showing the absence signal (rows 3 and 6). FIG. 4C shows that cells pretreated with A33-MORF (rows 2 and 5) followed by SWNT-cMORF-AF647 (rows 3 and 6), allowing for self-assembly at 37 8 C for up to 4 h, demonstrated a significant change in the distribution of the bound antibody with a change to scattered punctate staining. A similar pattern was observed for 30 min and 1 h incubations. High-power images are provided (rows 4,5 and 6). FIG. 4D shows that cells treated with anti-A33-MORF (rows 2 and 5) followed by cMORF-AF647 (rows 3 and 6) alone did not demonstrate a change in distribution of A33 about the cell membrane. High-power images are provided (rows 4,5 and 6). Anti-A33-MORF was evenly distributed about the plasma membrane, and cMORF-AF647 co-localized with the targeted mAb-MORF. FIG. 4E shows composite staining of conditions in rows 2 and 3 in FIG. 4C.

FIG. 5A is a flow cytometric analysis of CD20-positive, CD33-negative Daudi-GFP cells collected from mice treated with either isotype control anti-CD33-MORF or tumour-specific anti-CD20-MORF. Data show the shift in median fluorescence from untreated Daudi-GFP cells (representative mice are shown). FIG. 5B is a representative flow cytometric histograms of data in FIG. 5A showing untreated cells (front peak), isotype mAb-MORF treated cells (middle peak), and specific mAb-MORF treated cells (back peak). FIG. 5C shows tumor to blood ratios (T:B) for LS174T tumored mice pretargeted with either specific anti-A33-MORF or isotype control anti-CD33-MORF followed by injection of SWNT-cMORF-$^{111}$In(DOTA). Signal measurements in % ID per gram were measured at 4 or 24 h post-injection of SWNT-cMORF-$^{111}$In(DOTA). There was a significant increase (p<0.05) in tumor accumulation of the SWNT-cMORF-$^{111}$In(DOTA) at the tumor site only pre-targeted with specific antibody compared to isotype control. FIG. 5D shows the ratio of activity±SD of tumor-specific and isotype pre-targeted antibodies followed by second step SWNT-cMORF-$^{111}$In(DOTA) treatment at 24 hours on off-target tissues (n=4) 24 hours post treatment.

FIG. 6A shows whole animal weights of tumor-free mice treated with varying dose levels of $^{225}$Ac labeled SWNT-cMORF-DOTA. An additional group of mice received 450 nCi of free $^{225}$Ac as a control. Data reflect average weights, n=5 for all groups. Animal deaths are noted by an asterisk. FIG. 6B is a Kaplan-Meier plot of pre-annealed single-step treatment mouse survival with comparison to not annealed 1,800 nCi group from a. The toxicity study was halted at 40 days. Median survival was less than 2 weeks in all groups. FIG. 6C shows averaged organ weights of surviving mice sacrificed at 140 days post exposure to SWCNT-cMORF-$^{225}$Ac(DOTA) organized by treatment group.

DETAILED DESCRIPTION OF THE INVENTION

Figure 1A:
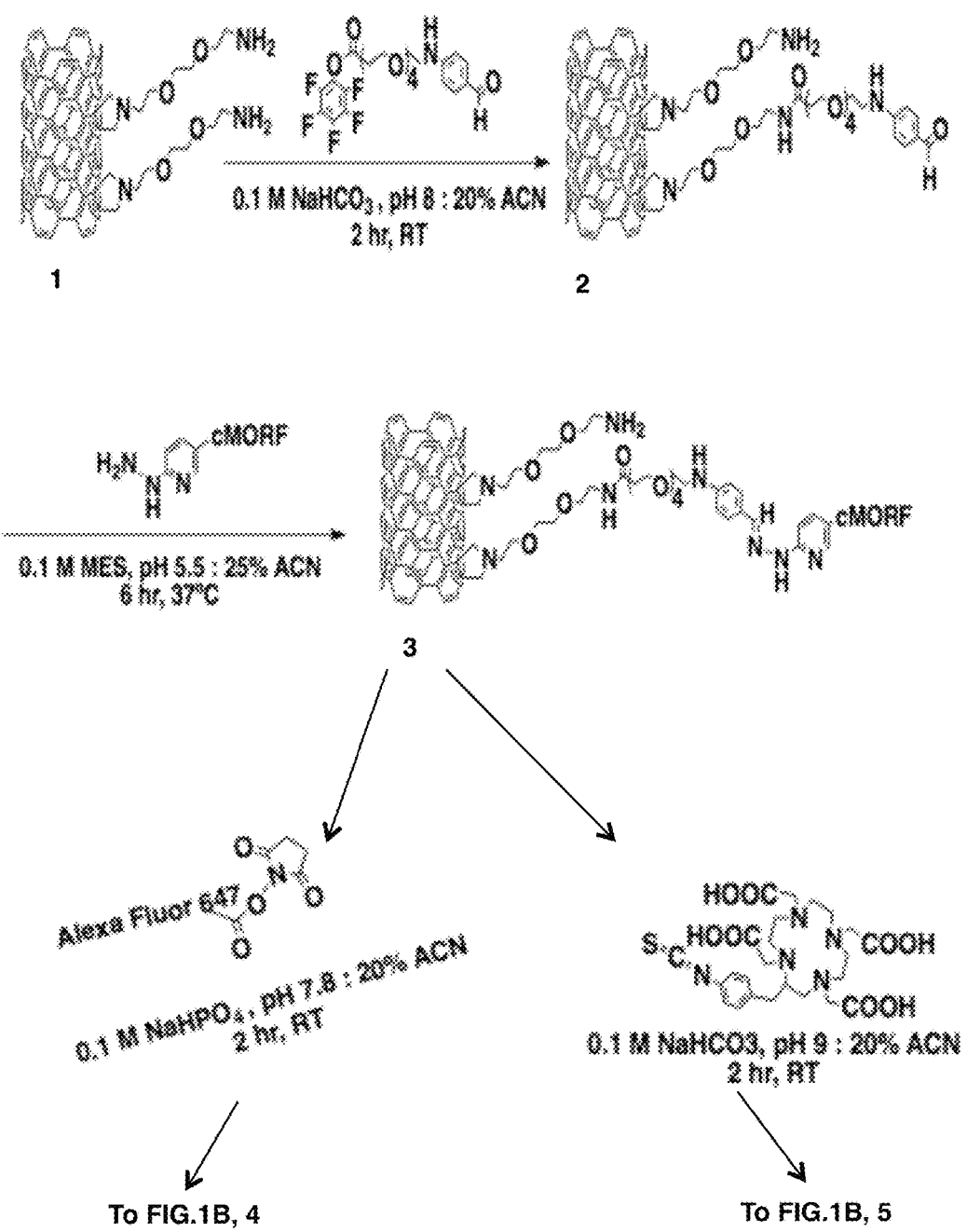
FIGS. 1A-1D depict the design and HPLC characterization of self-assembling SWNT-cMORF constructs.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

As used herein, the term "or" in the claims refers to "and/or" unless explicitly indicated to refer to alternatives only or the alternatives are mutually exclusive, although the disclosure supports a definition that refers to only alternatives and "and/or".

As used herein "another" or "other" may mean at least a second or more of the same or different claim element or components thereof. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "contacting" refers to any suitable method of bringing one or both of the two components comprising a self-assemblying single wall nanotube system, as described herein, into contact with a cell or an antigen comprising the same. In vitro or ex vivo this is achieved by exposing the cell to the components in a suitable medium. For in vivo applications, any known method of administration is suitable.

As used herein, the term "SWNT" refers to a single wall nanotube (SWNT) that has a functional pendant moiety or handle, such as a sidewall amine or aldehyde carbonyl, suitable for bioconjugation.

As used herein, the terms "MORF" and "cMORF" refer to a synthetic DNA analog with a morpholino backbone or morpholino oligonucleotide. The sequence of a cMORF oligonucleotide is complementary to that of a MORF oligonucleotide. As such, the terms "mAB-MORF" or "MORF-mAB" refers to a morpholino oligonucleotide linked to a monoclonal antibody via standard chemical methods.

As used herein, "M*" refers to a chelatable radiometal or other radionuclide or a chelatable contrast agent such as a nonradioactive nuclide useful as therapeutics for or diagnostics of a pathophysiological condition, for example, a cancer. As such, "M*-DOTA" refers to a radiometal chelated to the bifunctional chelator (4-isothiocyanatobenzyl)-1,4,7,10-tetraazacyclododecane-1,4,7,10-tetraacetic acid (DOTA) or diethylenetriaminepentaacetic acid (DTPA) which itself is directly linked to the SWNT.

As used herein, the term "SWNT-cMORF" refers to a single wall nanotube having a plurality of morpholino oligonucleotides with sequences complementary to the MORF oligonucleotides comprising a mAB-MORF oligonucleotide. As such, the term "SWNT-(cMORF-(mAB-MORF))" refers to a self-assembled complex in which the cMORF oligonucleotide is hybridized to the MORF oligonucleotide.

As used herein, SWNT-(M*DOTA)-(cMORF-(mAB-MORF))" refers to the self-assembled SWNT-(cMORF-(mAB-MORF)) complex in which the single wall nanotube also comprises a radiometal or other radionuclide or chelatable contrast agent linked to the SWNT via the bifunctional chelator (4-isothiocyanatobenzyl)-1,4,7,10-tetraazacyclododecane-1,4,7,10-tetraacetic acid (DOTA) or diethylenetriaminepentaacetic acid (DTPA).

As used herein, the term "subject" refers to any recipient of the SWNT self-assemblying components or SWNT constructs as described herein.

In one embodiment of the present invention there is provided a method of delivering a molecule in situ to a cell of interest, comprising contacting the cell with a first component comprising a morpholino oligonucleotide linked to a targeting moiety selective for the cell; contacting the morpholino oligonucleotide linked to the cell of interest via the targeting moiety with a second component comprising a soluble single wall nanotube construct having a plurality of morpholino oligonucleotides complementary to the targeting moiety-linked morpholino oligonucleotide and a plurality of the molecules (M*) independently linked to the single wall nanotube, said molecules comprising a deliverable payload; and hybridizing the morpholino oligonucleotide to the complementary morpholino oligonucleotide to form a self-assembled soluble single wall nanotube complex at the cell; wherein after hybridization the payload molecules are delivered in situ to the cell. In an aspect of this embodiment the in situ delivering step may comprise capping antigens located on the targeted cell via the self-assembled SWNT-mAB complex; and internalizing the complex into the cell.

In this embodiment upon self-assembly of the single wall nanotube complex, antigens located on the targeted cell may be capped and the in situ delivering step may comprise internalizing the complex into the cell. Also, both the morpholino oligonucleotide and the complementary morpholino oligonucleotides may be 18-mer oligonucleotides. Particularly, the morpholino oligonucleotide may have the sequence shown in SEQ ID NO: 1 and the complementary morpholino oligonucleotide may have the sequence shown in SEQ ID NO: 2.

Also in this embodiment, the targeting moiety may be a monoclonal antibody or fragment thereof or a small molecule ligand each selective for a cell associated with a solid or a disseminated cancer. In one aspect the monoclonal antibody may be an anti-CD20, anti-CD33, or anti-A33 monoclonal antibody or a single chain variable fragment (scFv) or fragment antigen-binding (Fab) fragment thereof. In another aspect the monoclonal antibody itself may be the payload molecule delivered in situ. In yet another aspect the small molecule ligand may be a folate receptor ligand or an Arg-Gly-Asp peptide. Representative examples of a cancer are a lymphoma, a leukemia or a colon cancer.

In addition, the payload molecule may be one or both of a diagnostic molecule or a therapeutic molecule. The molecule may be a radionuclide linked to the SWNT via a bifunctional chelator. Representative examples of a bifunctional chelator are (4-isothiocyanatobenzyl)-1,4,7,10-tetraazacyclododecane-1,4,7,10-tetraacetic acid (DOTA) or diethylenetriaminepentaacetic acid (DTPA). In one aspect the diagnostic molecule may be indium-111, copper-64, iodine-124, iodine-131, yttrium-86, a gadolinium contrast agent, a manganese contrast agent, or a fluorophore. In another aspect the therapeutic molecule may be actinium-225, astatine-211, technetium-99, lutetium-177, gallium-68, holmium-166, bismuth-212, bismuth-213, yttrium-90, copper-67, samarium-117, samarium-153, iodine-123, iodine-125, or iodine-131.

In another embodiment of the present invention there is provided a method for diagnosing a cancer in a subject, comprising administering sequentially to the subject a first component of a self-assembled single wall nanotube complex having a targeting moiety, selective for a cell associated with the cancer, conjugated to a morpholino oligonucleotide and a second component thereof comprising a single wall nanotube construct having a plurality of complementary morpholino oligonucleotides and of diagnostic payload molecules independently conjugated thereto; and detecting the diagnostic payload molecules in the subject after self-assembly of the first and second components of the complex at the cancer-associated cell, thereby diagnosing the cancer.

In this embodiment the first component morpholino oligonucleotides may have a sequence shown in SEQ ID NO: 1 and the second component complementary morpholino oligonucleotides may have a sequence shown in SEQ ID NO: 2. Also, the targeting moiety may be a monoclonal antibody or fragment thereof or a small molecule ligand. Representative examples of the monoclonal antibody or fragment thereof and the small molecule ligand are as described supra. In addition the diagnostic payload may be linked to the single wall nanotube via a bifunctional chelator. In addition, the bifunctional chelators and the cancers are as described supra. Furthermore, the diagnostic payload molecule may be indium-111, copper-64, iodine-124, iodine-131, yttrium-86, a gadolinium contrast agent, a manganese contrast agent, or a fluorophore.

In this embodiment the cell of interest may be a cell associated with a cancer in a subject. In one aspect the deliverable payload may comprise molecules diagnostic of the cancer, where the method further comprises detecting the diagnostic payload molecules after in situ delivery thereof to the cancer-associated cell in the subject, thereby diagnosing the cancer. In another aspect, the deliverable payload may comprise molecules therapeutic against the cancer, where the method further comprises treating the cancer with the therapeutic molecules after in situ delivery thereof to the cancer-associated cell in the subject. In all embodiments and aspects thereof, the cancer may be a lymphoma, a leukemia or a colon cancer.

In yet another embodiment of the present invention there is provided a method for treating a cancer in a subject, comprising administering sequentially to the subject a first component and a second component of a self-assembled single wall nanotube complex functionalized with a targeting moiety and one or more therapeutic payload molecules independently linked to morpholino oligonucleotides; where the first and second components self-assemble on a cell associated with the cancer that is targeted by the targeting moiety, thereby delivering the therapeutic payload to the cell to treat the cancer.

In one aspect the first component of the self-assembled SWNT complex may comprise a first morpholino oligonucleotide conjugated to the targeting moiety. The first morpholino oligonucleotide may have a sequence shown in SEQ ID NO: 1. In another aspect the second component of the self-assembled single wall nanotube complex may comprise a plurality of second morpholino oligonucleotides having a sequence complementary to the first morpholino oligonucleotide and a plurality of the payload molecules independently linked to the soluble single wall nanotube. The second complementary morpholino oligonucleotide may have a sequence shown in SEQ ID NO: 2.

In all embodiments and aspects thereof upon self-assembly of the complex, antigens located on the cancer-associated cell may be capped and the complex may be internalized into the cell. Also, the therapeutic payload may be a radionuclide linked to the single wall nanotube via a bifunctional chelator. A representative example of a bifunctional chelator is as described supra. The therapeutic radionuclide may be actinium-225, astatine-211, technetium-99, lutetium-177, gallium-68, holmium-166, bismuth-212, bismuth-213, yttrium-90, copper-64, copper-67, samarium-117, samarium-153, iodine-123, iodine-125, or iodine-131. Alternatively, the monoclonal antibody may be the therapeutic payload molecule. The targeting moiety, including monoclonal antibodies or fragments thereof and small molecule ligands and the cancers are as described supra In yet another embodiment of the present invention there is provided a self-assembly single walled nanotube complex, comprising a first component having a morpholino oligonucleotide linked to a monoclonal antibody or a fragment thereof; and a second component having a plurality of complementary morpholino oligonucleotides and a plurality of one or both of a diagnostic or therapeutic molecules each independently linked to the single wall nanotube.

In this embodiment the diagnostic and therapeutic molecules may be a radionuclide linked to the single wall nanotube via a bifunctional chelator, such as DOTA or DTPA, as described supra. Representative examples of the radionuclide are actinium-225, astatine-211, indium-111, technetium-99, lutetium-177, gallium-68, holmium-166, bismuth-212, bismuth-213, yttrium-86, yttrium-90, copper-64, copper-67, samarium-117, samarium-153, iodine-123, iodine-124, iodine-125, or iodine-131. In addition the monoclonal antibody may be the therapeutic molecule. Examples of a monoclonal antibody or fragment thereof may be an anti-CD20, anti-CD33, or anti-A33 antibody or a single chain variable fragment (scFv) or fragment antigen-binding (Fab) fragment thereof.

In yet another embodiment of the present invention there is provided a single wall nanotube construct comprising a plurality of a bifunctional chelator covalently linked to the single wall nanotube; a radionuclide chelated to each bifunctional chelator; and a plurality of morpholino oligonucleotides conjugated to the single wall nanotube. In this embodiment the bifunctional chelator and the radionuclide for a diagnostic or a therapetic molecule or a payload molecule are as described supra.

Provided herein are single wall nanotube constructs, systems and methods useful in multistep self-assembly approaches for delivering molecules or payloads to a cell. The conjugation of single-walled carbon nanotubes to morpholino oligonucleotide sequences (SWNT-cMORF) confers on them the ability to self-assemble with cancer-selective antibodies appended with complementary oligonucleotides (mAb-MORF) with sub-nanomolar affinity and in physiologic conditions. Self-assembly promotes target antigen complex internalization that enables delivery of diagnostic and/or therapeutic agents into cells via normally non-internalizing targets.

Generally, the self-assembly single wall nanotube (SWNT) system comprises two components. The first component comprises a morpholino oligonucleotide linked to a targeting moiety, such as a monoclonal antibody or fragment thereof or other targeting peptide or ligand. Preferably, the targeting moiety is a monoclonal antibody or a single chain variable fragment (scFv) or fragment antigen-binding (Fab) fragment thereof and the first component has the structure mAb-MORF or MORF-mAb. Alternatively, the targeting moiety may be a small molecule ligand, such as, but not limited to, an Arg-Gly-Asp (RGD) peptide or a folate receptor ligand. The targeting moiety may be linked to the morpholino oligonucleotide via standard chemical methods. Preferably, the targeting moiety will target a cell associated with a cancer.

The second component in the system comprises synthetic, covalently modified SWNTs bearing multiple copies of a synthetic oligonucleotide analog, for example, morpholino oligonucleotides (cMORF) and fluorophores and/or radioisotopes or other nuclides. The linkage between the SWNT and morpholinos (SWNT-cMORF) is spectroscopically quantifiable with about 5-15 morpholinos per 200 nm of SWNT. The SWNT-cMORF conjugates can self-assemble onto antibody targeted cancer cell surfaces with excellent specificity and high affinity via hybridization to the morpholino oligonucleotide MORF.

The morpholino oligonucleotide and its complement may be short oligonucleotides, such as an 18-mer oligonucleotide, for example, but not limited to, the complementary sequences in SEQ ID NOS: 1 and 2, as shown in Example 1. Morpholino oligonucleotides are less immunogenic (28) than protein based pairs. This allows for multiple administrations and potentially more complex multi-step self-assembling constructs, complexes and systems.

The multivalent self-assembly system can trigger antigen capping and internalization of mAb-MORF targets, even in otherwise surface stable antigens. This internalization may be a result of the capability of SWNT-cMORF to self-assemble with multiple mAb-MORF targets, mimicking cross-linking of surface receptors. The ability to trigger internalization of surface antigens through self-assembly of the system components may enhance therapeutic efficacy of agents appended to the SWNT. Thus, the second step in the self-assembly also may trigger internalization of the initial targeting agent thereby capturing the cytotoxic agent within the target cell and improving the therapeutic index.

As such, the self-assembly constructs, systems and complexes of the present invention are effective vehicles in methods for treating a pathophysiological state, such as a solid or a disseminated cancer. Representative solid and disseminated cancers may be, but not limited to, colon cancers, lymphomas and leukemias. Therapeutic radionuclides may be delivered to cancer cells using the SWNT-cMORF constructs. The therapeutic radionuclide may be, but not limited to, actinium-225, astatine-211, technetium-99, lutetium-177, gallium-68, holmium-166, bismuth-212, bismuth-213, yttrium-90, copper-67, samarium-117, samarium-153, iodine-123, iodine-125, or iodine-131.

Also, the self-assembly constructs, systems and complexes are useful for detecting and diagnosing a pathophysiological state or condition in vivo or in vitro in diagnostic assays. The SWNT-cMORF may comprise a contrast agent, a diagnostic radionuclide or a fluorophore linked to the SWNT. For example a diagnostic radionuclide may be, but not limited to, indium-111, copper-64, iodine-124, iodine-131, or yttrium-86. Other non-radionuclide diagnostic agents may be a gadolinium contrast agent, a manganese contrast agent or a fluorophore, as are known in the art. It is contemplated that superparamagnetic iron oxide based contrast agents also may be utilized as diagnostic agents in the methods and compositions provided herein.

The following examples are given for the purpose of illustrating various embodiments of the invention and are not meant to limit the present invention in any fashion.

EXAMPLE 1

Methods and Materials
Modification of SWNT

High purity (>90%) single walled carbon nanotubes were obtained from NanoLab Inc (Waltham, Mass.). These arc-discharge produced single-walled carbon nanotubes were reacted according to described protocols (33) to produce SWNT-NH$_2$. The SWNT-NH$_2$ product was purified on a C18 Seppak (Waters) by application and wash in 20% acetonitrile: 0.1 M triethyl amine acetate. The purified product was eluted with 50% acetonitrile:water. This solution was then lyophilized to give the dark brown SWNT-NH2 solid, or diluted directly into a bicarbonate buffer (0.1 M Na HCO3, pH 9). To the SWNT-NH2 was added 0.6 mmol/g of PEG4/PFB (Solulink) long chain crosslinker. This reaction was allowed to proceed for 2 hours at room temperature. The reaction mixture was then purified on a disposable benchtop 10-DG size exclusion column (Biorad), with elution of the aldehyde and amine bearing SWNT-4FB-NH$_2$ (2) product into a 0.1 M MES, 0.15 M NaCl, pH 5.5 buffer.

Conjugation of MORF and cMORF to Nanotubes and Antibodies

Morpholino oligonucleotides MORF (TCTTCTACT-TCACAACTA, SEQ ID NO: 1) and cMORF (TAGTTGT-GAAGTAGAAGA, SEQ ID NO: 2) were custom synthesized (Gene Tools Inc.), and contained primary amines on the 3' end. The primary amine was capped with either an aldehyde or hydrazine moiety for conjugation to the antibodies or nanotubes, respectively. The MORF-NH$_2$/cMORF-NH$_2$ were reacted with a 20-fold excess of succinimidyl 4-formyl benzoate (Thermo Scientific) or succinimidyl hydrazinonicotinamide (Thermo Scientific) in a 0.1 M sodium bicarbonate buffer containing 20% acetonitrile. Free linker was removed through gel-filtration chromatography on a 10-DG column (Bio-Rad) and the morpholinos were purified into a buffer of 0.1 M MES, 0.15 M NaCl, pH 5.5.

The cMORF-HyNic was mixed with SWNT-4FB-NH$_2$ at a ratio of 0.2 mmol of cMORF per gram of single-walled carbon nanotubes in a buffer of 0.1 M MES, 0.15 M NaCl, pH 5.5 containing 25% acetonitrile. The reaction was allowed to proceed at 37° C. for 6 hours, and then at room temperature overnight with shaking. The SWNT-cMORF-NH$_2$ product was purified by washing on a C18 Seppak (Waters) with 25% acetonitrile in 0.1 M TEAA. The product was eluted with 50% acetonitrile:water and then lyophilized to give the solid product. The product was verified to be free of cMORF-HyNic by reverse phase C18 HPLC.

Monoclonal antibodies HuM195 (Lintuzumab; Sloan-Kettering)/anti-CD33, Rituximab/anti-CD20 (Genentech), and huA33/anti-A33 (Ludwig Institute) were diluted into a modification buffer of 0.1 M sodium phosphate, 0.15 M NaCl, pH 7.6. A 10 to 15 fold excess of succinimidyl hydrazine nicotinamide was added slowly to the antibody solutions. The antibodies were reacted for 2 hours followed by purification on a 10-DG gel filtration column. The hydrazone modified mAbs (mAb-HyNic) were eluted into 0.1 M MES, 0.15 M NaCl, pH 5.5. The mAb-HyNic were then reacted with the aldehyde modified MORF-4FB at a ratio of 8 MORF per antibody and reacted at room temperature for at least 12 hours with gentle shaking. The remaining free MORF-4FB was removed by purification on a 100,000 MWCO centrifugal filter device (Amicon Ultra, Millipore), with at least three washes in PBS. Protein was quantified through the D$_C$ protein assay (Biorad) and attached morpholinos were quantified spectroscopically by the bis-aryl hydrazone chromophore ($\lambda_{max}$=354 nm). The purity of the mAb-MORF conjugates were verified by HPLC on a Superdex 200 column.

Radiolabeling

The SWNT-cMORF-NH$_2$ was dissolved in a buffer of 0.1 M sodium bicarbonate previously treated with Chelex 100 resin (Bio-Rad) to render the buffer free of divalent metals. To this solution was added a ratio of 10 mmol/g of amine reactive 2-(4-isothiocyanatobenzyl)-1,4,7,10-tetraazacyclododecane-1,4,7,10-tetraacetic acid (DOTA-SCN, Macrocyclics). This reaction was kept at room temperature for 2 hours followed by purification on a 10-DG gel-filtration column previously treated with 25 mM DTPA to render the stationary phase metal free. The product was eluted in metal-free distilled H$_2$O and lyophilized to give the solid SWNT-cMORF-DOTA product. This product was radiolabeled with $^{111}$InCl$_3$ (MDS Nordion) by addition of radioisotope in an ammonium acetate buffer (1M), pH 5, containing 20% acetonitrile for a period of 0.5 hours at 50° C. The labeling mixture was quenched by addition of 50 mM DTPA and purified on a 10-DG gel filtration column into PBS. The radiochemical purity was measured by instant thin layer chromatography using mobile phases of 10 mM EDTA and 0.9% NaCL/10 mM NaOH (8). ITLC strips were counted using a System 400 Imaging Scanner (Bioscan, Inc.) Radiochemical purity was >90% across 5 repeated labeling reactions and was confirmed by radio-detection on HPLC. The cMORF-DOTA construct used in comparative binding assays was similarly labeled with $^{111}$In (0.8 Ci/g) and alternatively with $^{225}$Ac (0.66 Ci/g). Radiochemical purity was quantitative.

HPLC Assays

All high performance liquid chromatography was performed on a System Gold Bioessential 125/168 diode-array detection instrument (Beckman Coulter) equipped with an in-line gamma-RAM model 3 radioactivity detector (IN/US). Analysis was performed using both 32 Karat chromatography software (Beckman Coulter) and Prism graphing and analysis software (Graphpad). Gel filtration chromatography was performed on a Superdex 200 column in a 20 mM sodium acetate, 0.15 M sodium chloride, pH 6.5 isocratic mobile phase. Reverse phase HPLC was performed on a Gemini C18 column (Phenomenex) with a gradient of 20% acetonitrile in 0.1 M tetraethyl ammonium acetate (TEAA) to 100% acetonitrile. For antibody-nanotube hybridization assays, samples were mixed in phosphate buffered saline, unless otherwise noted, in 150 µL total volume for 5 minutes prior to injection onto the HPLC column.

Confocal Microscopy

LS174T cells were seeded onto tissue culture treated, poly-lysine coated, multi-well chambered slides (Nunc) for 24 hours at 50,000 cell/mL. The slides were treated with 10 nM of one of anti-A33-MORF, anti-A33, or control anti-CD19-MORF antibodies for 4 hours at 37° C. The unbound antibody was then washed out, and cells were treated with media alone, media containing 7.5 µg/mL SWNT-cMORF-AF647 conjugates, or media containing 100 nM fluorescently labeled cMORF-AF647. The cells were then incubated at 37° C. for up to 4 hours. At specified time points (30 min, 1 hr, 4 hrs), the cells were washed with PBS and fixed with 4% neutral buffered paraformaldehyde. To visualize anti-A33 antibodies, cells were permeabilized with a buffer of PBS containing 0.5% BSA and 0.2% Triton-X, then stained with a 1:500 dilution of Alexa Fluor 488 labeled anti-human IgG (Invitrogen). After staining, cells were washed and mounted in Prolong Gold medium containing a DAPI nuclear stain (Invitrogen). SWNT-cMORF and cMORF could be directly visualized through the appended AF647 fluorophores. Imaging was performed on a laser scanning confocal imaging system (Leica), with settings maintained across visualization of the different cell treatment conditions.

Cell Binding

The Daudi B-cell lymphoma, LS174T colon adenocarcinoma, and HL60 promyelocytic leukemia cell lines were obtained from the ATCC and cultured in RPMI containing 10% FBS at 37° C. in 5% CO$_2$. GFP transfected Daudi were produced through retroviral transfection as described previously (9). Prior to flow cytometric assays cells were suspended in ice cold phosphate buffered saline (PBS) containing 2% human serum as a blocking agent, or, where noted, 100% human serum. Suspension cultures were washed by centrifugation and resuspension, while adherent cells were trypsinized in 0.05% tryspin containg EDTA (Gibco) followed by washing. Cells in suspension were first bound with mAb-MORF at 10 nM for 1 hour, either on ice or at 37° C. Following mAb-MORF treatment, cells were washed with binding buffer, and then bound with SWNT-cMORF-AF647 conjugates at a range of concentrations up to 10 μg/mL. Cells were washed by centrifugation/resuspension and read on an Accuri C6 flow cytometer (Accuri, Inc.). Data were processed using Flojo analysis software (TreeStar, Inc.). A second cell binding assay was conducted to compare cMORF-DOTA and SWNT-cMORF-DOTA second steps. These methodologies were identical except instead of a fluorophore, either $^{111}$In or $^{225}$Ac labeled DOTA was assayed on a Cobra II gamma counter (Packard).

In Vivo Binding Studies

All mice were female NCl nu/nu, 4-6 weeks old, and all animal studies were conducted under the approval of the Institutional Animal Care and Use Committee. To assess binding in the Daudi lymphoma model, Daudi cells were cultured in suspension, followed by washing with cold PBS and resuspension in 0.9% NaCl (Hospira, Inc.). Mice were then injected with 20 million cells per mouse. After 6 hours, the mice were then treated with 3 μg of morpholino conjugates of either Daudi specific anti-CD20 Rituximab (anti-CD20-MORF) or isotype control anti-CD33 HuM195 (anti-CD33-MORF). 16 hours later, mice were then injected i.p. with 2 μg of SWNT-cMORF-AF647. The SWNT-cMORF-AF647 was allowed to circulate and target for 4 hours, after which mice were sacrificed and the lymphoma cells collected by lavage of the i.p. cavity with ice cold PBS. This cell suspension was washed with PBS, passed through a cell strainer to remove debris, and run on a Accuri C6 flow cytometer. The cell suspension was gated for Daudi-GFP cells in the FL1 channel and then fluorescence of SWNT-cMORF-AF647 was measured in the FL4 channel. Data were analyzed on FloJo cytometry software (TreeStar, Inc.).

For solid tumor studies, 4-6 week old female NCl nu/nu mice were xenografted with 5 million LS174T cells subcutaneously into the right flank. Cells were suspended in a 1:1 mixture of Matrigel matrix (BD) and ice cold PBS. Once tumors reached ~150 mm³, at about 7 days, mice were treated with i.p. injection of 20 μg of either tumor specific anti-A33-MORF or isotype control anti-CD33-MORF antibodies diluted in normal saline. 72 hours after treatment with the antibodies, the mice were injected with 12 μg of SWNT-cMORF-$^{111}$In(DOTA) intravenously via the retroorbital sinus. Isoflurane anesthesia was administered with a vaporizing chamber (VetEquip). Typical specific activity of SWNT-cMORF-$^{111}$In(DOTA) was ~2-3 Ci/g and a total activity of 24-36 μCi per mouse was administered. At various time points mice were sacrificed, their organs harvested and weighed, and the radioactivity was counted on a Cobra II gamma counter (Packard).

Biodistribution

SWNT-cMORF-DOTA were labeled with $^{111}$In at 99.7% radio-chemical purity as previously described. 30 BALB/c mice (NCl Labs), age 4-6 weeks, were randomized into 6 groups of 5 mice each. Each mouse was injected I.P. with 3200 nCi of SWNT-cMORF-$^{111}$In(DOTA) in 200 uL of sterile normal saline. Mice were sacrificed at 1, 4, 8, 12, and 24 hours. Bedding from the cages containing excreted urine and feces were collected for quantification. Kidneys, lungs, muscle, heart, blood, liver, spleen, intestine, and bone were harvested from sacrificed mice and the % injected dose for each organ was quantified as previously described.

In Vivo Toxicology Study in Mice: SWNT-cMORF-DOTA

SWNT-cMORF-DOTA were labeled with $^{225}$Ac at a 98.4% radio-chemical purity. 45 BALB/c mice (NCl Labs,) age 4-6 weeks. Mice were randomly divided into 9 groups of 5 mice and received a single injection as shown in Table 1.

TABLE 1

| Cage Number | I.P. injection (200 uL) |
|---|---|
| 1 | Saline |
| 2 | SWNT-cMORF-DOTA (0 nCi $^{225}$Ac) (17 μg) |
| 3 | SWNT-cMORF-DOTA (450 nCi $^{225}$Ac) (2.83 μg) |
| 4 | SWNT-cMORF-DOTA (900 nCi $^{225}$Ac) (5.66 μg) |
| 5 | SWNT-cMORF-DOTA (1350 nCi $^{225}$Ac) (8.5 μg) |
| 6 | SWNT-cMORF-DOTA (1800 nCi $^{225}$Ac) (11.3 μg) |
| 7 | SWNT-cMORF-DOTA (2250 nCi $^{225}$Ac) (14.2 μg) |
| 8 | SWNT-cMORF-DOTA (2700 nCi $^{225}$Ac) (17 μg) |
| 9 | Unchelated $^{225}$Ac (1350 nCi $^{225}$Ac) (3.57 μg) |

Bedding was collected in full from each group at 10 hours to determine elimination. Each group was visually assessed and weighed regularly over 140 days at which time the liver, spleen, bone marrow, and kidneys of each mouse were submitted for histological analysis. Hematoxylin and eosin (H&E) staining of paraffin-embedded tissue sections was performed according to standard protocols. Histological evaluation was performed by a veterinary pathologist blinded to the treatment groups.

Toxicology Study in Mice: Pre-Annealed Ab-MORF-SWNT-cMORF-DOTA ($^{225}$Ac)

SWNT-cMORF-DOTA were labeled with $^{225}$Ac at a 99.6% (post dialysis workup) radio-chemical purity. Anti-CD20 antibodies (Rituximab), were labeled with MORF at 0.9 per antibody to stem crosslinking. SWNT-cMORF-($^{225}$Ac)DOTA were placed in a 20,000 MWCO dialysis cassette with a MORF to cMORF excess of Ab-MORF (Rituximab). This was allowed to stir in metal free water for 6 hours, replacing water twice, before collection of the annealed product by syringe. HPLC confirmed annealing. 35 BALB/c mice (NCl Labs), age 5-7 weeks. Mice were randomly divided into 7 groups of 5 mice and received a single injection as shown in Table 2. Mice were followed until death or weight stabilization had occurred. Injected masses denote mass of complete construct, though up to one equivalent mass of excess, unbound Ab-MORF was also injected in groups 3-7.

TABLE 2

| Cage Number | I.P. injection (200 uL) |
|---|---|
| 1 | Saline |
| 2 | Ab-MORF (50 ug) |
| 3 | Ab-MORF-SWNT-cMORF-DOTA (0 nCi $^{225}$Ac) (~24 ug) |
| 4 | Ab-MORF-SWNT-cMORF-DOTA (450 nCi $^{225}$Ac) (~6 ug) |
| 5 | Ab-MORF-SWNT-cMORF-DOTA (900 nCi $^{225}$Ac) (~12 ug) |
| 6 | Ab-MORF-SWNT-cMORF-DOTA (1350 nCi $^{225}$Ac) (~18 ug) |
| 7 | Ab-MORF-SWNT-cMORF-DOTA (1800 nCi $^{225}$Ac) (~24 ug) |

In Vivo Therapy Study in Mice

SWNT-cMORF-DOTA were labeled with $^{225}$Ac at a 96% radio-chemical purity. The Morpholino-tagged rituximab (3.5 MORF per antibody) was produced as previously detailed. Binding selectivity of the reagents was confirmed in vitro using $^{111}$In labeled SWNT-cMORF-DOTA as a the reporter in a cross control with HL60 cells and morpholino tagged Hum195 (3.74 MORF per antibody). CB17SC-F SCID mice (Taconic Labs,) age 5-7 weeks, were injected I.P. with 20 million firefly-luciferase expressing Daudi lymphoma cells in 200 μL PBS. After one week, the mice were imaged to confirm growth of tumor in all mice to be used in the therapy experiment using an IVIS 200 Imaging System (Caliper Sciences). Images were performed 5 min after an IP injection of 200 μL of 5 mg/mL luciferin.

The mice were then randomly assigned into 10 treatment groups of 5 mice each that received two sequential injections at 0 and 24 hours as shown in Table 3.

TABLE 3

| Group | Injection 1, 0 h (200 uL) | Injection 2, 24 h (200 μL) |
|---|---|---|
| 1: Untreated control | Saline | Saline |
| 2: Anti-CD20 alone control | 1.5 ug anti-CD20-MORF | Saline |
| 3: Unlabeled SWNT Control | Saline | SWCNT-cMORF-DOTA (0 nCi $^{225}$Ac) (3.57 μg) |
| 4: Isotype control | 1.5 ug anti-CD33-MORF | SWCNT-cMORF-DOTA (333 nCi $^{225}$Ac) (1.19 μg) |
| 5: Isotype control | 1.5 ug anti-CD33-MORF | SWCNT-cMORF-DOTA (666 nCi $^{225}$Ac) (2.38 μg) |
| 6: Isotype control | 1.5 ug anti-CD33-MORF | SWCNT-cMORF-DOTA (999 nCi $^{225}$Ac) (3.57 μg) |
| 7: Treatment group | 1.5 ug Anti-CD20-MORF (Rituximab) | SWCNT-cMORF-DOTA (333 nCi $^{225}$Ac) (1.19 μg) |
| 8: Treatment group | 1.5 ug Anti-CD20-MORF (Rituximab) | SWCNT-cMORF-DOTA (666 nCi $^{225}$Ac) (2.38 μg) |
| 9: Treatment group | 1.5 ug Anti-CD20-MORF (Rituximab) | SWCNT-cMORF-DOTA (999 nCi $^{225}$Ac) (3.57 μg) |
| 10: Blocked treatment group Dual control | 1.5 ug Anti-CD20-MORF (Rituximab) | MORF Blocked SWCNT-cMORF-DOTA (999 nCi $^{225}$Ac) |

Mice were imaged and photons quantitated for tumor burden on day 3, 6, 9 and 15. Data were analyzed using Igor Pro Living Image software Version 2.60 (Wavemetrics.)

EXAMPLE 2

Oligonucleotide Modification and Radiolabeling of SWNT

The amine functionalized single-walled carbon nanotubes (FIG. 1A, 1) used herein were prepared from high purity arc-produced single-walled carbon nanotubes or HiPCO SWNT via covalent cycloaddition of azomethine ylides as described (27-28). This reaction attaches hydrophilic chains to the single-walled carbon nanotubes sidewalls that could be terminated with primary amines to serve as the attachment site for bifunctional radiometal chelates, fluorophores, and the morpholino oligonucleotide complementary to a modified antibody (cMORF).

Constructs averaged 350 nm in length by DLS (Zetasizer Nano Zs system equipped with a narrow bandwidth filter (Malvern Instruments)) and TEM (EM-201 (Philips)) with diameter of approximately 1.2 nm giving 12 carbon atoms per 2.5 angstroms. They were characterized by Raman spectroscopy (InVia micro Raman system (Renishaw)).

In order to append the morpholinos to both the targeting antibodies and the carbon nanotubes, a chemical approach that produces a spectrally quantifiable bis-aryl hydrazone linkage between the two entities was chosen (6, 29). The side-wall amines on the single-walled carbon nanotubes were reacted with an activated ester of an aromatic aldehyde linker at a sub-stoichiometric ratio to introduce a number of aldehydes onto the SWNT-NH$_2$ sidewalls. The product 2 (FIG. 1A) was then analyzed for amine content by a quantitative ninhydrin assay (30) which showed that approximately half of the amines remained un-reacted, (1.1 reacted:1 unreacted, starting with 1.1 mmol/L primary amines). Based on amine to carbon molar ratios (discounting the weight of SWNT covalent adducts) the level of substitution is approximately 1 addition per 289 carbons or approximately 125 morpholino adducts per SWNT of median length (348.9 nm). The average unmodified and modified nanotube molecular weights (434,968.20 g/mol, ~1.22E6 g/mol) derivation is provided as follows and assumes a SWNT with a diameter of 1 nm and length of 348.9 nm determined by dynamic light scattering.

For an unmodified tube: (1 nm/0.245 nm)(3.1414)(2 carbon atoms)=25.64 carbons around the circumference. For every 0.283 nm length, there are 4×25.64=102.58 carbon atoms. (100 nm/0.283 nm)(102.58)(12.01)=434,068.20 Amu.

For a modified tube bearing ~125 morpholino adducts: ~6317 Amu×125=789625 Amu. 789625+434968=1.22×10$^6$ Amu.

The incorporated aromatic aldehydes were quantified by reaction with 2-hydrazino pyridine to form a spectrally quantifiable chromophore of $\lambda_{max}$=350 nm. This reaction confirmed that the reacted amines had been converted to reactive aldehyde linker groups at an approximate 50% yield.

Figure 1B:
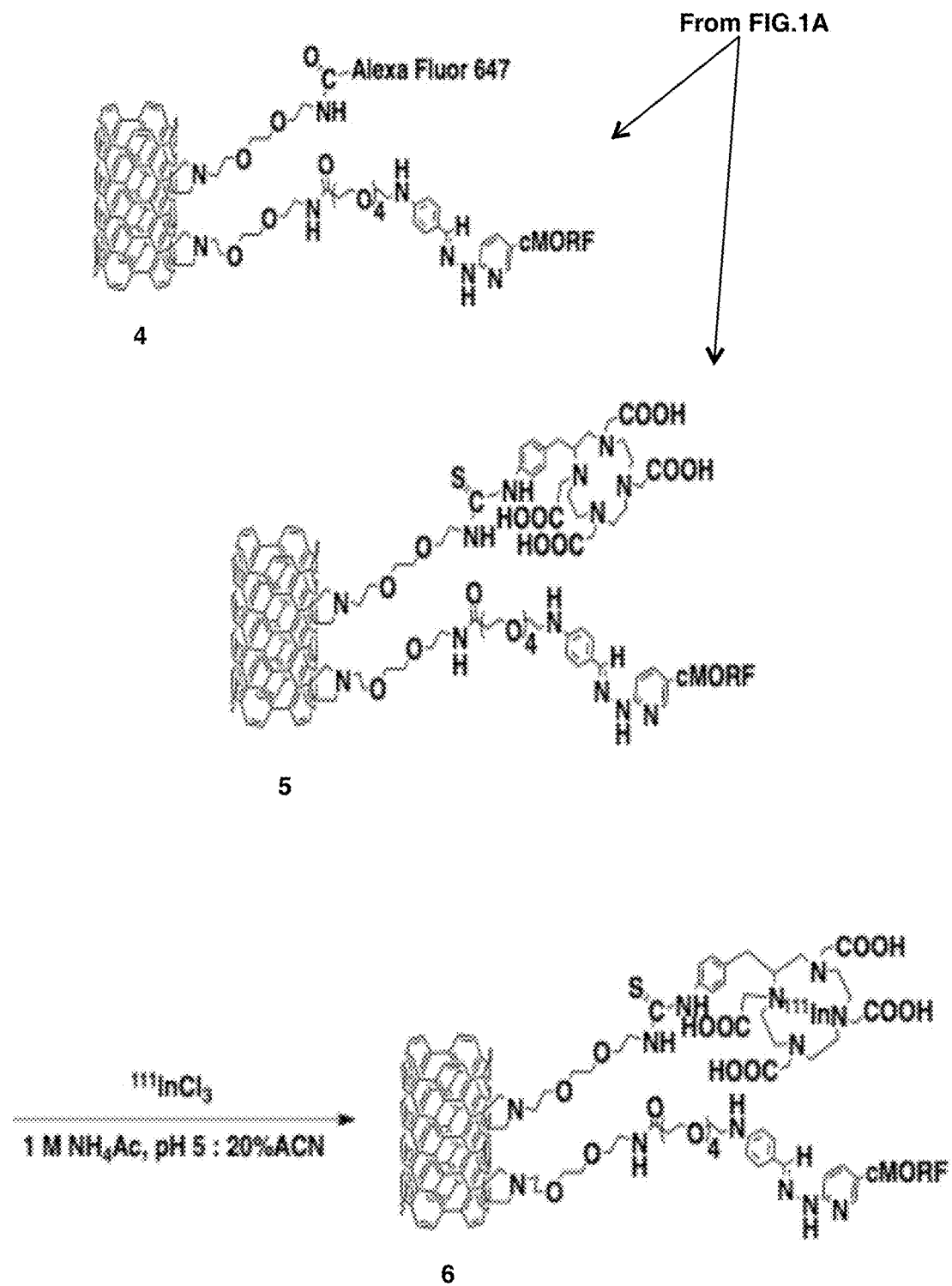

Custom synthesized morpholinos, with sequences chosen based on previous pretargeting literature (31), bearing 3' primary amines (cMORF, sequence: TAG-TTG-TGA-AGT-AGA-AGA; SEQ ID NO: 2) were reacted with a 20-fold excess of succinimidyl hyzdrazino nicotinamide at pH 9 and purified via gel filtration chromatography to yield the cMORF-HyNic product. The cMORF-HyNic was coupled with the aldehyde functionalized single-walled carbon nanotubes at pH 5.5 to yield the SWNT-cMORF conjugate 3 (Fig. A). The remaining amines in compound 3 were then either capped with the radiometal chelating moiety, (4-isothiocyanatobenzyl)-1,4,7,10-tetraazacyclododecane-1,4,7,10-tetraacetic acid (DOTA), for subsequent labeling with radiometals (FIG. 1B, 5), or reacted with the activated ester of Alexa Fluor 647 to introduce a fluorescent label for microscopy and cytometric assays (FIG. 1B, 4). The modification of post-morpholino-addition SWNT with DOTA or Alexa Fluor 647 was run with stoichiometric excess of the new adduct. This reaction consumed all remaining amines to yield 1 DOTA or Alexa Fluor per 316 carbon atoms or approximately 115 adducts per median-length tube (discounting the weight of SWNT covalent adducts).

The DOTA chelator was labeled with isotopes befitting their intended use. The gamma emitting isotope $^{111}$In was used for biodistribution and binding studies. Single-walled carbon nanotubes also were labeled with $^{225}$Ac, an alpha-particle emitting cytotoxic isotope, for application in therapeutic models. The DOTA functionalized material 5 was radiolabeled with $^{111}$InCl$_3$. The radiolabeled product 6 was typically produced with ~95% radiochemical purity. Using this synthetic approach, SWNT-cMORF conjugates of high specific activities, up to 25 Ci/g, were produced when labeling with $^{111}$In. When labeling SWNT-cMORF-DOTA, 5, with varying amounts of $^{225}$Ac, specific activities up to 2 Ci/g were achieved. This represents a greater than 100-fold improvement in specific activity of the SWNT-cMORF compared to monoclonal antibodies (10, 32) of similar molecular weight, and demonstrates the potential for signal amplification with highly multivalent single-walled carbon nanotubes scaffolds.

Figure 1C:
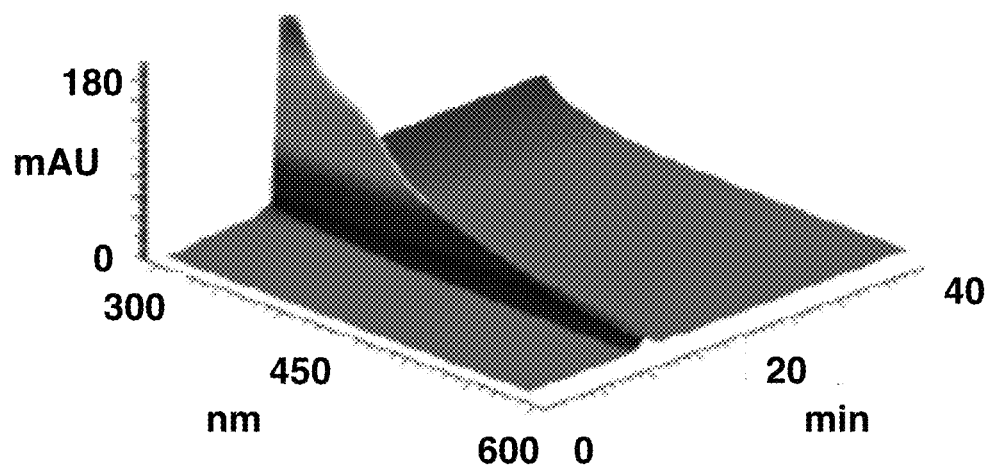

HPLC of constructs 4, 5, and 6 in both reverse phase and gel permeation systems demonstrated high purity and the single peak observed had a spectrum consistent with single-walled carbon nanotubes appended with bis-aryl hydrazone linkages of $\lambda_{max}$=354 nm (FIG. 1C). The Raman spectrum of the amine functionalized SWNTs, 1, was consistent with highly modified SWNTs, demonstrating a rise in the disorder band at 1360 cm–1 and a broad major tangential mode peak at 1580 $cm^{-1}$, as in previous studies (8).

Figure 1D:
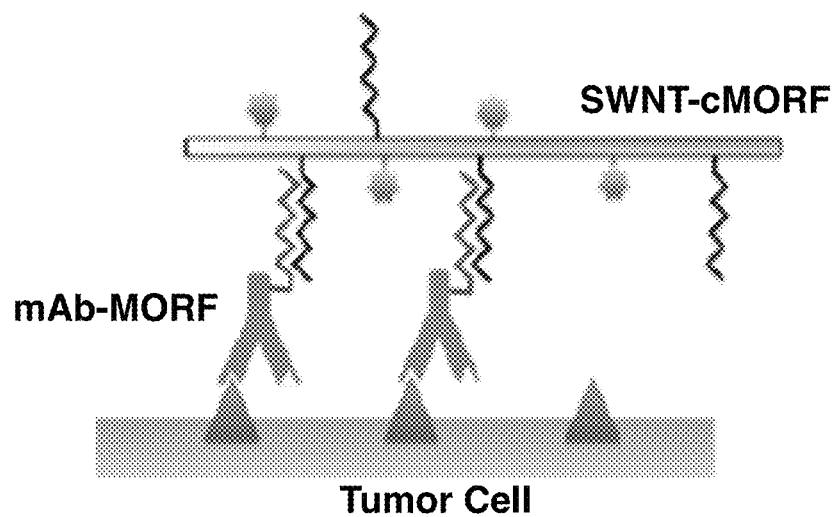

Antibodies were coupled to morpholino oligonucleotides complementary to the sequence on the nanotubes via similar reaction chemistry to that implemented for the nanotube conjugation. Four different antibody-MORF conjugates were produced, anti-CD33-MORF (Lintuzumab, 3.75 MORF per Ab), anti-CD20-MORF (Rituximab, 3.5 MORF per Ab), and anti-CD and anti-A33-MORF (huA33). All three antibodies are of the human IgG1 isotype and are extensively used in human therapies. This approach to attachment of morpholino oligos to antibodies has been described (29) and typically resulted in 3 to 6 morpholinos per antibody, regardless of the antibody type. The product antibody-morpholino conjugates (mAb-MORF) were >95% purity, as measured by size-exclusion HPLC. FIG. 1D is a diagram of SWNT-cMORF self-assembly onto mAb-MORF targeted tumor cells.

EXAMPLE 3

SWNT-cMORF Hybridizes with Multiple Different mAb-MORF In Vitro and in the Presence of Serum at 37°

Figure 2A:
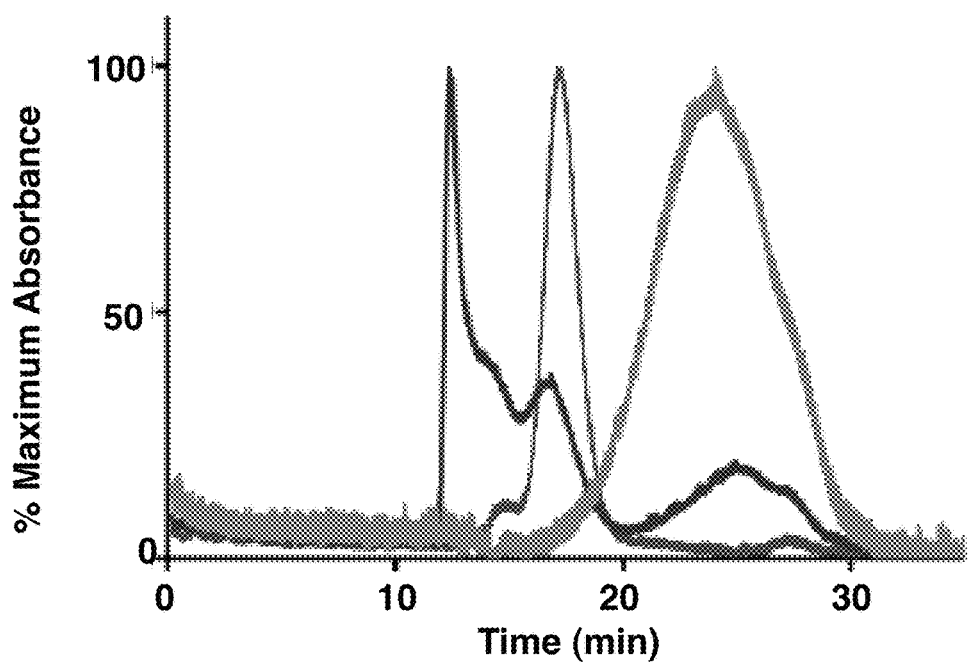
FIG. 2A-2E depict that SWNT-cMORF hybridizes with multiple mAb-MORF in vitro and in the presence of serum.
Figure 2B:
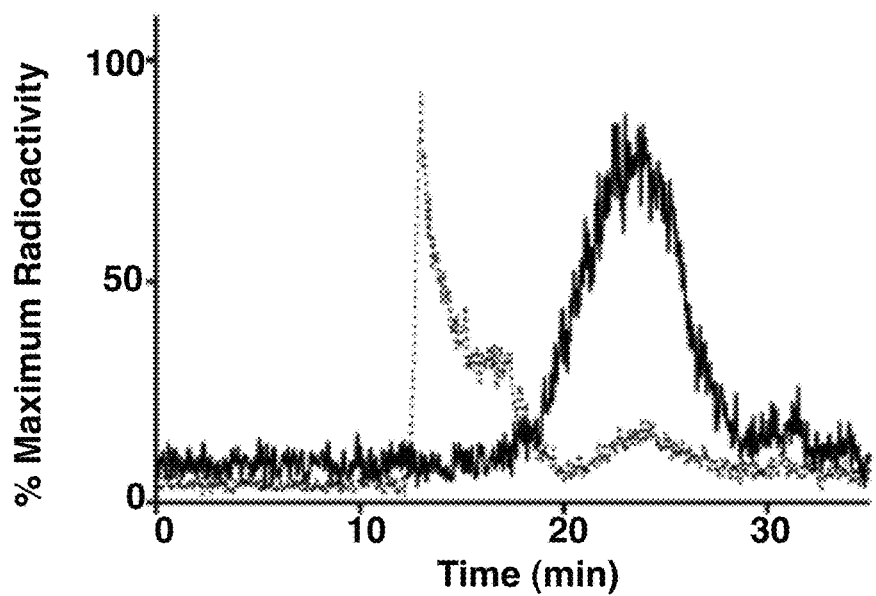
Figure 2C:
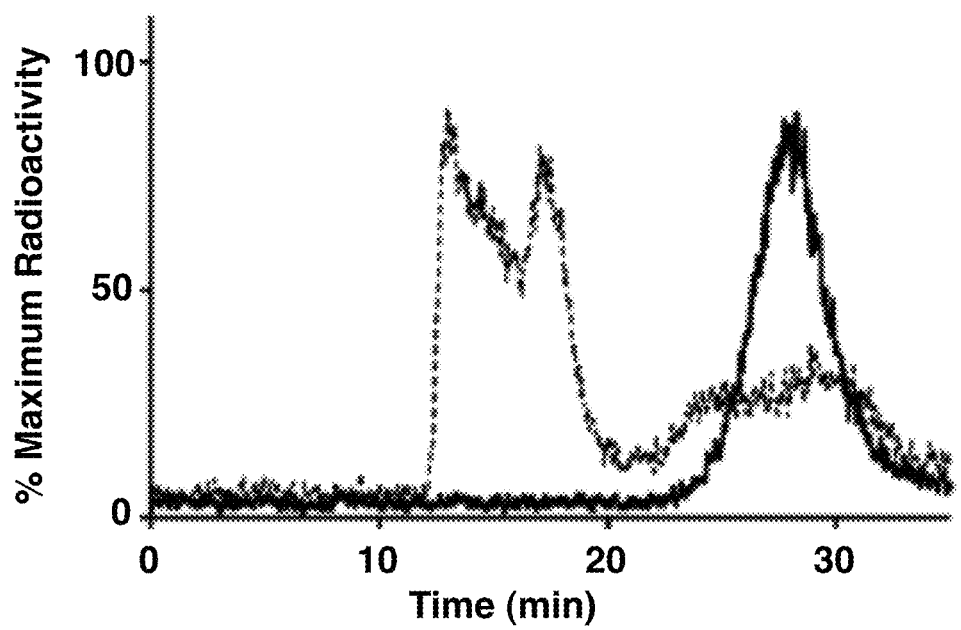

Hybridization of the antibody-MORF onto the SWNT-cMORF conjugate could be monitored through HPLC (FIGS. 2A-2D). The mAb-MORF conjugates alone had an elution time of approximately 18 minutes, which was consistent with a molecular weight of ~150,000 Da based on protein standards. When the mAb-MORF, anti-CD20-MORF and anti-A33-MORF, was incubated with the complementary SWNT-cMORF construct, the nanotube elution shifted to a high-molecular-weight band and eluted at the void volume at 12 min. (FIG. 2B). The column's molecular weight cutoff is 600 kDa, suggesting that multiple antibodies were hybridizing to the single-walled carbon nanotubes to form large, but still soluble, multimeric constructs (FIG. 2A).

Figure 2D:
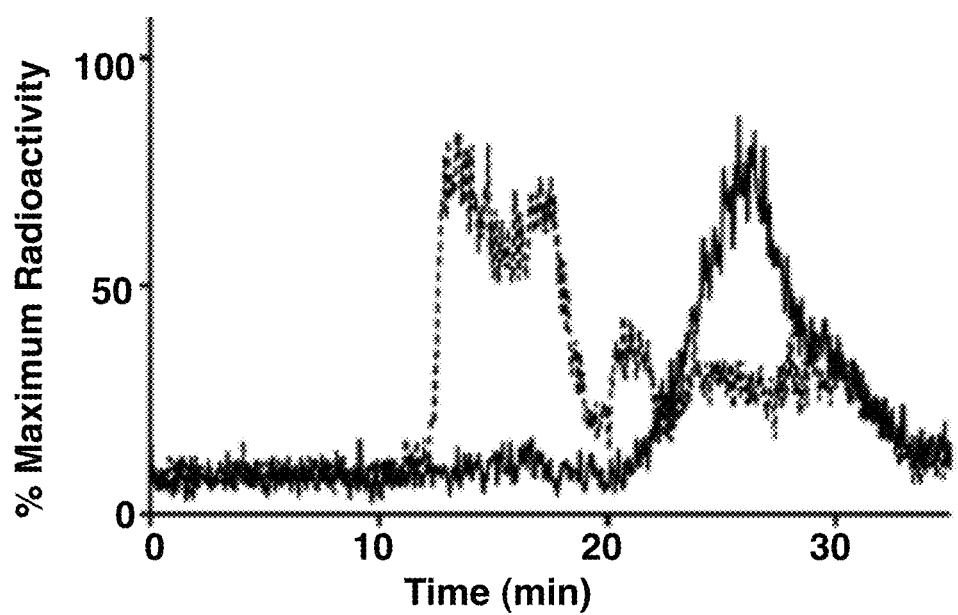
Figure 6A:
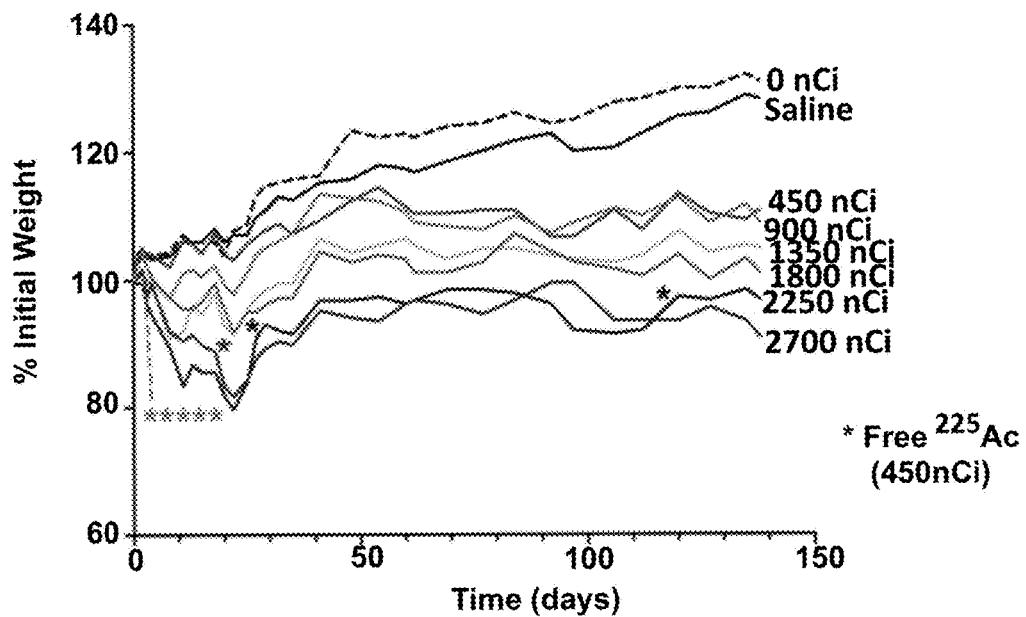
FIGS. 6A-6C shows that SWNT-cMORF-$^{225}$Ac(DOTA) mitigates radioisotope toxicity and can be used as an effective agent in multistep therapy of disseminated lymphoma.

In order to specifically monitor the elution of the SWNT-cMORF through an appended label, a similar experiment was performed with radiolabeled SWNT-cMORF-$^{111}$In (DOTA) (FIG. 2B, 6), and the elution of the isotope was monitored with an HPLC radiodetector which showed an identical pattern of results for SWNT-cMORF mixed with both anti-CD20-33 MORF and anti-A33-MORF. This confirmed that the assembly of these complexes is independent of the antibody used (FIG. 2C) and the presence of 100% human serum at 37° C. (FIG. 2D). The dependence of the observed phenomenon on MORF/cMORF hybridization was demonstrated by blocking the nucleotide hybridization sites of the Ab-SWNT complex by addition of excess free cMORF.

Figure 2E:
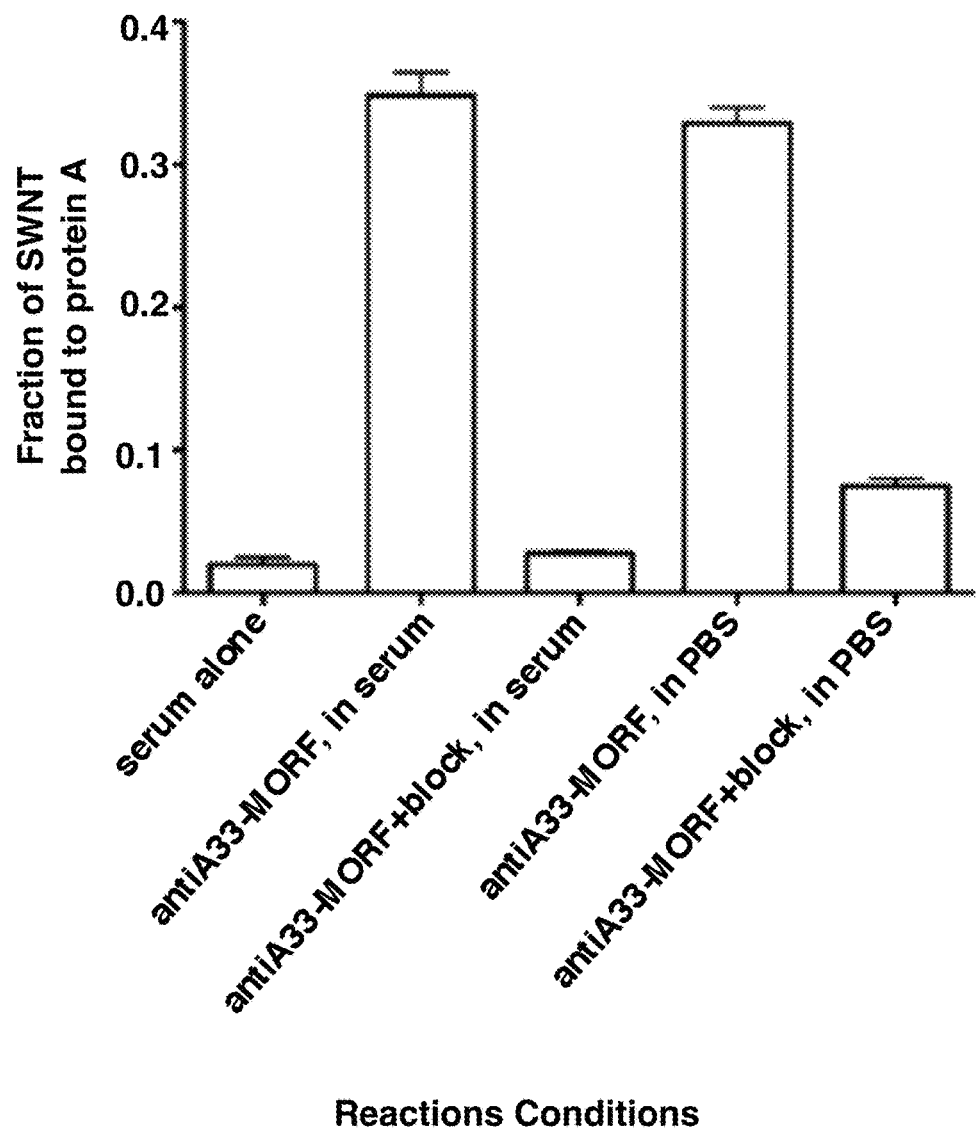

Another approach to assay the hybridization of the SWNT-cMORF-$^{111}$In(DOTA) conjugate and complementary mAb-MORF was to capture the radiolabeled SWNT-cMORF with protein A beads after addition of mAb-MORF (FIG. 2E). Because protein A selectively binds IgG, the labeled SWNT-cMORF should be immobilized on the agarose beads only when annealed to the IgG. Indeed, when radiolabeled SWNT-cMORF conjugates were incubated with protein A beads alone, only 1% of the nanotubes were captured by beads. However, when complementary mAb-MORF was previously added to the SWNT-cMORF, ~35% of the nanotubes were captured by the beads. This binding to the beads could be completely blocked by addition of excess cMORF to block nanotube hybridization sites on the antibody. This hybridization could occur and be maintained in the presence of 100% serum at 37° C. for 24 hours. Nearly identical binding was obtained under these conditions as compared to binding buffer (PBS with 1% BSA), demonstrating again that serum and temperature had little to no effect on the nanotube-antibody hybridization.

The efficiency of hybridization was unaffected by serum, and could be blocked by an addition of excess free cMORF. Isocratic, aqueous mobile phase elution of the SWNT-cMORF conjugate in the HPLC size-exclusion column (Superdex 200) occurred as a late, broad band. The delayed elution, despite the high single-walled carbon nanotubes molecular weight, is attributable to the highly anisotropic geometry of the SWNT, which is known to significantly retard elongated macromolecules in common gel (9, 33). This peak had spectral features consistent with SWNT. It was found that if mAb-MORF (anti-CD20-MORF or anti-CD33-MORF) and SWNT-cMORF were mixed together at micro-molar concentrations for 12 h at 4° C., they formed sub-millimeter, visible aggregates. Neither SWNT-cMORF alone, nor mAb-MORF alone at 10× this concentration, showed any aggregation. When the macrostructures were administered to cells, these aggregates showed no targeted binding enrichment in a cross control with HL60 or Daudi cells. This suggested that due to the multivalent nature of the SWNT-cMORF, extensive cross-linking had occurred, perturbing the ability to bind to multiple cells, or resist washes before flow cytometric analysis.

EXAMPLE 4

Self-Assembly on Pretargeted Cells

SWNT-cMORF self-assembled onto tumor cell surfaces that were bound specifically by mAb-MORF conjugates containing the complementary oligonucleotide sequence. Three different cancer cell lines, Daudi (B-cell lymphoma), HL60 (promyelocytic leukemia) and LS174T (colon adenocarcinoma), pretargeted by anti-CD20 (Rituximab), anti-CD33 (Hum195), and anti-A33 monoclonal antibodies, respectively, were used. All antibodies were human IgG1 isotype. The cells were incubated with either specific or isotype control antibody-MORF, followed by treatment with fluorescently labeled SWNT-cMORF (FIG. 1B, 4). As a control, cells targeted with specific mAb-MORF conjugates were blocked with excess cMORF prior to the addition of SWNT-cMORF. The binding of fluorescently labeled single-walled carbon nanotubes was quantified as the change in median fluorescence intensity as measured by flow cytometry.

The single-walled carbon nanotubes self-assembled onto all three cell types with excellent specificity (FIGS. 3A-3D). Furthermore, the binding was significantly abrogated when blocked with excess cMORF and there was little binding to cells treated with isotype control mAb-MORF. Binding also was tested across a range of conditions, at temperatures of 4° C., 25° C., and 37° C. as well as in 100% human serum. Similar binding was obtained regardless of the binding conditions, confirming that MORF/cMORF hybridization onto cells can occur in serum at 37° C.

Figure 3A:
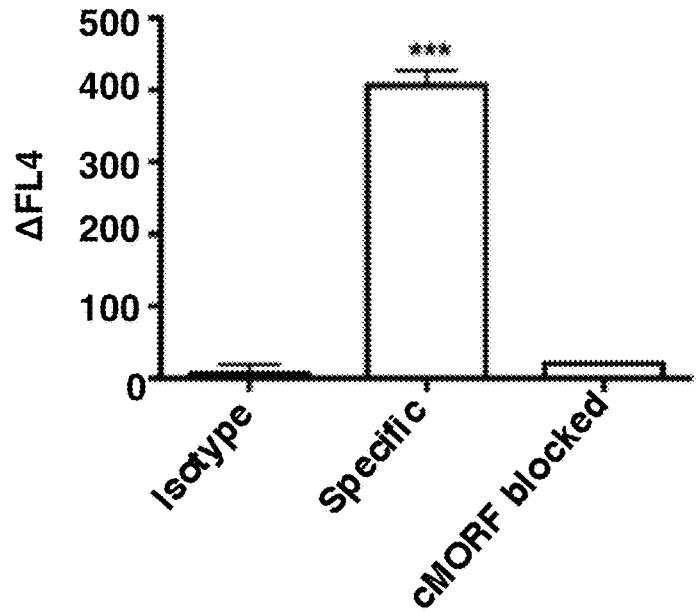
FIGS. 3A-3E depict the self-assembly of SWNT-cMORF onto tumor cells pretargeted with mAb-MORF is highly specific and high affinity.
Figure 3B:
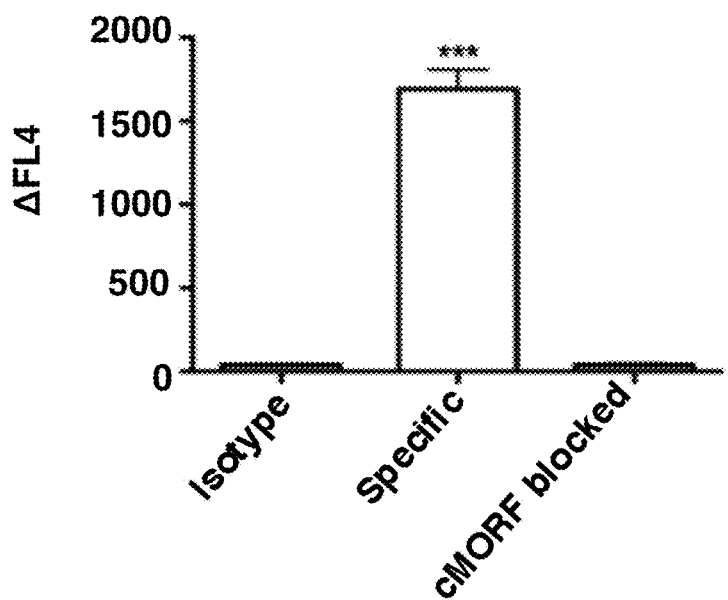
Figure 3C:
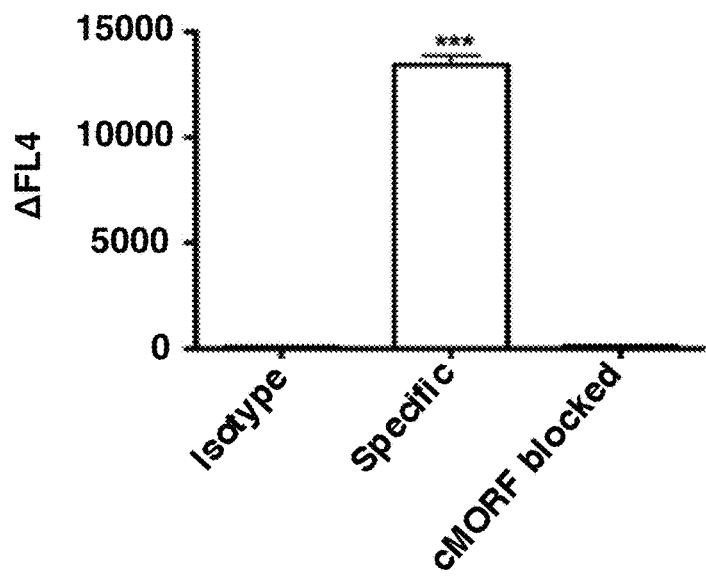
Figure 3D:
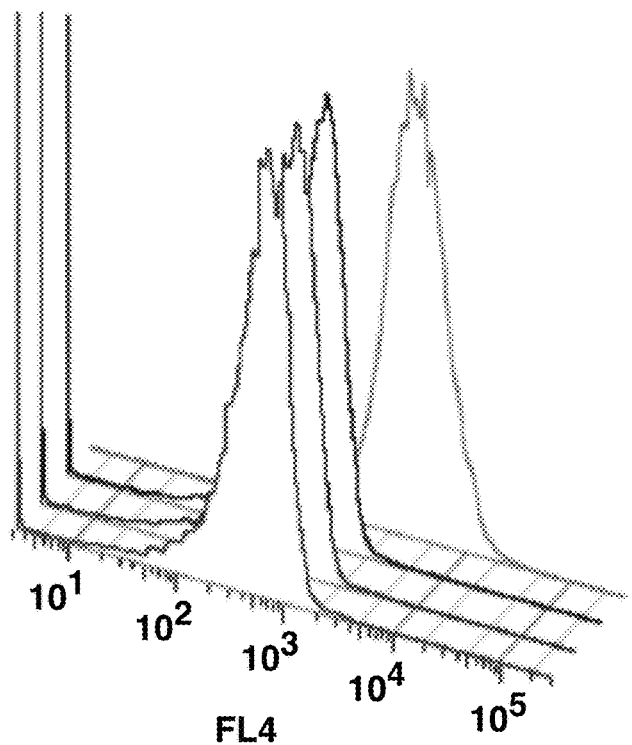
Figure 3E:
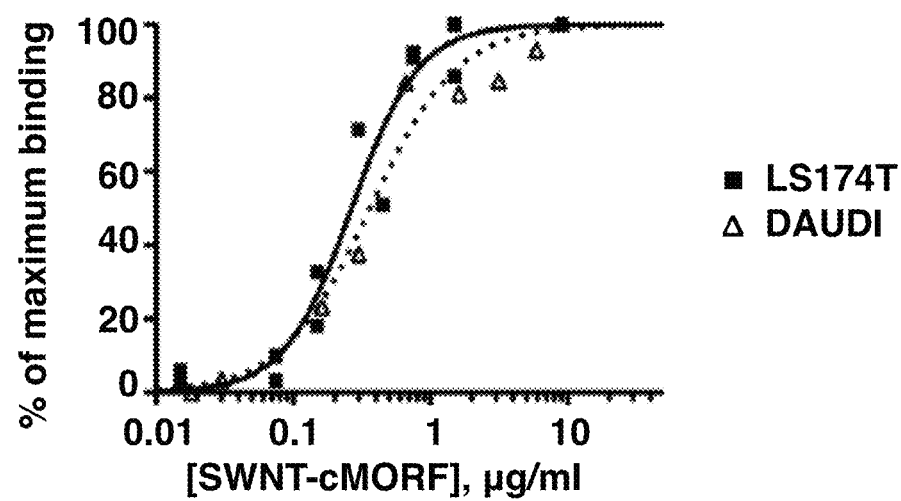

To test the affinity of the interaction between the SWNT-cMORF and the cells pre-targeted with mAb-MORF, a similar binding study was performed (FIG. 3E). After subtraction of the non-specific binding, calculated using isotype control anti-CD33-MORF, the shift in median fluorescence was plotted as a function of the SWNT-cMORF concentration. An avidity estimation was performed targeting Daudi cells with anti-CD20-MORF, HL60 cells with anti-CD33-MORF and LS174T with anti-CD33-MORF. The result was a characteristic sigmoid binding curve, with an apparent dissociation constant of 0.3 µg/mL. With the expected molecular weight of the SWNT-cMORF constructs of 350-500 kDa, this apparent affinity represents a dissociation constant of ~0.6 nM. This affinity was identical for the three different cell types, demonstrating that the affinity of the SWNT-cMORF for the mAb-MORF was independent of the chosen cancer target or targeting vehicle.

EXAMPLE 5

Self-Assembly on Cells Leads to Capping and Internalization

After demonstration of self-assembly of SWNT-cMORF onto tumor cells, the fate of the self-assembled SWNT-(cMORF-(mAB-MORF)) complexes on the cell surface was determined. A series of confocal microscopy studies was performed to track anti-A33 antibodies and anti-A33/single-walled carbon nanotubes complexes after binding to the LS174T cells. Plated cells were treated with anti-A33 or anti-A33-MORF, washed, and incubated at 37° C. in culture medium for up to 24 hours.

Figure 4A:
FIGS. 4A-4E demonstrate that SWNT-cMORF conjugates are able to induce antigen capping and internalization when self-assembled onto cells targeted with mAb-MORF.
Figure 4B:
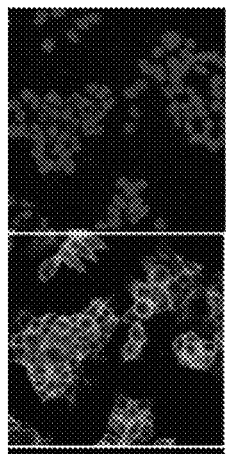
Figure 4C:
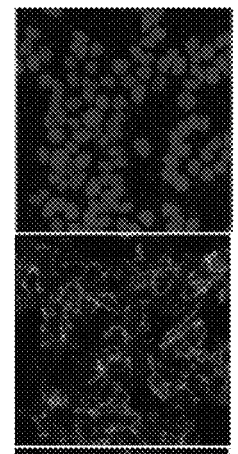

When cells were treated with the anti-A33 antibody alone (green), the antibody was stable on the cell surface for up to 24 hours (FIG. 4A). A33 was chosen for this demonstration due to stable surface expression of A33 glycoprotein after anti-A33 antibody binding, its slow internalization and lysosomal degradation with a turnover of 6 weeks at 37° C. (34) similar to CD20 as used in the therapy studies. The antibody was evenly distributed along the membrane. Likewise, the anti-A33-MORF antibody conjugate alone was stable on the cell surface and remained evenly distributed (FIG. 4B). There was no binding of an isotype control antibody (anti-CD19-MORF). However, when SWNT-cMORF (pink) was added to anti-A33-MORF pre-targeted cells, followed by up to 4 hours of incubation at 37° C. a dramatic change was observed in the distribution of antibody in the target cells (FIGS. 4C, 4E) including clustering of the self-assembled mAb-MORF/SWNT-cMORF complexes on the cell membrane, leading to punctate staining suggestive of antigen capping. Addition of SWNT-cMORF to cells that were targeted with control antibodies (anti-A33 without MORF or isotype control anti-CD19-MORF) did not result in any change in staining pattern and no binding of SWNT-cMORF to the control antibody treated cells was observed.

Figure 4D:
Figure 4E:

Furthermore, in cells treated with mAb-MORF followed by SWNT-cMORF the appearance of antibody and nanotube positive, punctate structures were observed inside the cells (FIG. 4D). This clustering phenomenon was evident 30 minutes after addition of SWNT-cMORF constructs, and intracellular staining continued to increase through the 4 hours assayed. These images suggest an endocytic uptake of the anti-A33-MORF/SWNT-cMORF complexes upon self-assembly into multimeric surface structures separate from internalization of individual A33 molecules. Therefore, as SWNT-cMORF constructs can bind multiple antibodies on the cell surface, this cross-linking apparently leads to promotion of rapid intracellular delivery of the complexes in line with observations of crosslinking upon prolonged mixing of SWNT-cMORF and Ab-MORF (FIGS. 1A-1D), a desired, but unexpected effect.

To test this hypothesis, anti-A33-MORF targeted cells were treated with free cMORF oligonucleotides, which should not bind multiple antibodies. When cells pretreated with anti-A33-MORF were subsequently treated with fluorescently labeled cMORF alone, the staining profile of the cMORF was completely co-localized with the antibody and the pattern of surface binding was unchanged from antibody alone (FIG. 4D, compare with FIGS. 4A-4B). This result suggests that the capping and internalization phenomenon depended on the multivalency of the second step.

EXAMPLE 6

Self-Assembly In Vivo in Mice

Having demonstrated that the SWNT-cMORF can self-assemble onto specific cancer cells in vitro, this activity was assessed next in live mice. This was initially performed in a CD20-positive Daudi lymphoma model. SCID mice were injected with Daudi-GFP (9) cells i.p, followed 24 hours later with injection of either lymphoma specific anti-CD20-MORF or anti-CD33-MORF isotype control. The mice were treated 24 hr later with fluorescently labeled SWNT-cMORF. After a further 6 hours, the mice were sacrificed, the lymphoma cells were harvested and the cell suspension was analyzed by flow cytometry. The Daudi-GFP cells were tracked by gating for green positive cells and then assayed for the fluorescence of the SWNT-cMORF-Alexa Fluor 647 in the FL4 channel. The SWNT-cMORF bound selectively to the tumor cells in mice pretargeted with specific antibody as evidenced by the 20-fold increase in the median fluorescence intensity of the gated Daudi cells was observed in the FL4 channel (FIGS. 5A-5B) from the control anti-CD20 mAb-MORF treated animal, confirming specific binding to the target in the harvested cells. The isotype control antibody treated animals did not demonstrate binding or self-assembly.

It also was demonstrated that this approach is feasible with systemically administered constructs in a solid carcinoma model in which tumor penetration of each of the components would be more difficult. A subcutaneous, xenografted, solid tumor LS174T colon adenocarcinoma model was chosen. The anti-A33 antibody tumor targeting in this model was separately tested via positron emission tomography of 1-124 labeled anti-A33. This demonstrated that, by 72 hours after injection, the antibody reaches ~10% ID/g in the tumor and was reduced to ~4% ID/g in the bloodstream (tumor to blood ratio of ~2.5).

These relative concentrations are sufficient for administration of the SWNT-cMORF-($^{111}$In)DOTA second step at 72 hours after mAb-MORF. Following treatment with i.v. injection of SWNT-cMORF-($^{111}$In)DOTA, the accumulation of SWNT-cMORF-($^{111}$In)DOTA in the blood, tumor, and muscle were quantified at 4 and 24 hours. As in previous biodistribution studies with functionalized single-walled carbon nanotubes constructs, the SWNT-cMORF-($^{111}$In) DOTA rapidly cleared the bloodstream with levels of 1.4% ID/g and 0.26% ID/g at 4 and 24 hours, respectively. There was no significant difference in blood levels between experimental treatment and the isotype control group.

Figure 5A:
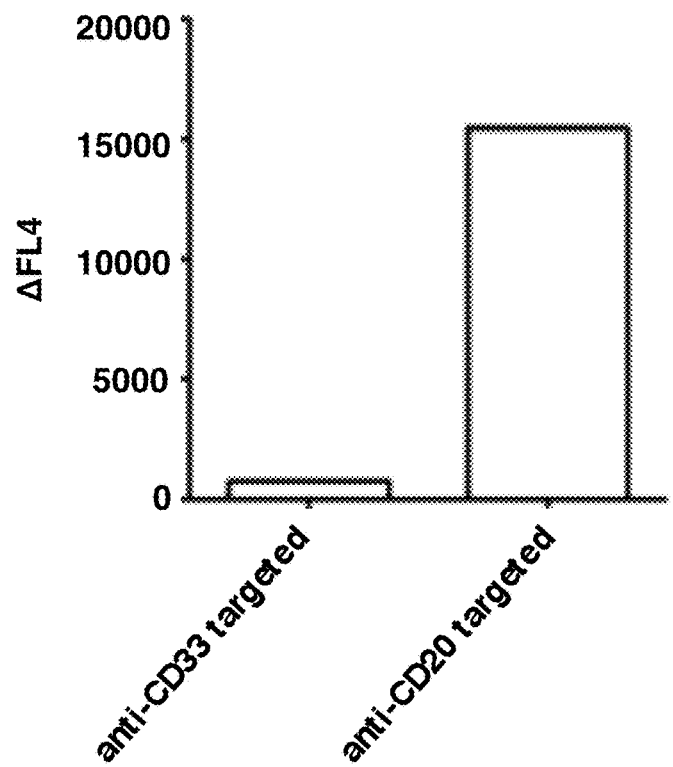
FIGS. 5A-5D depict that SWNT-cMORF can selectively self-assemble onto pretargeted tumors in vivo.
Figure 5B:
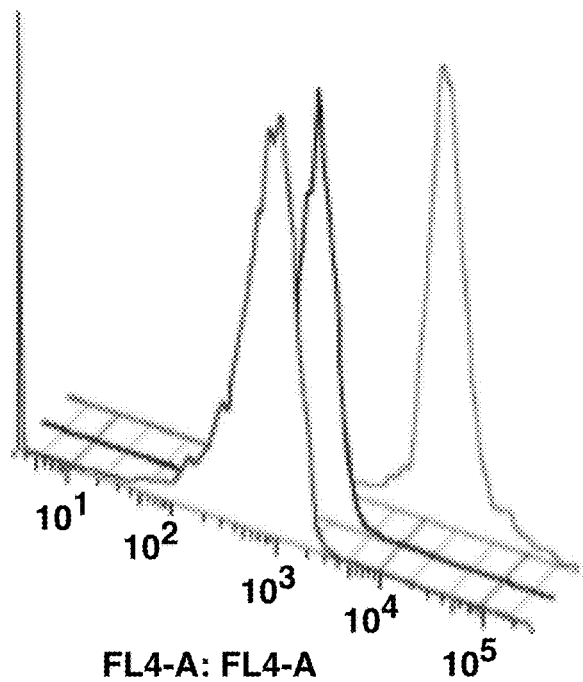
Figure 5C:
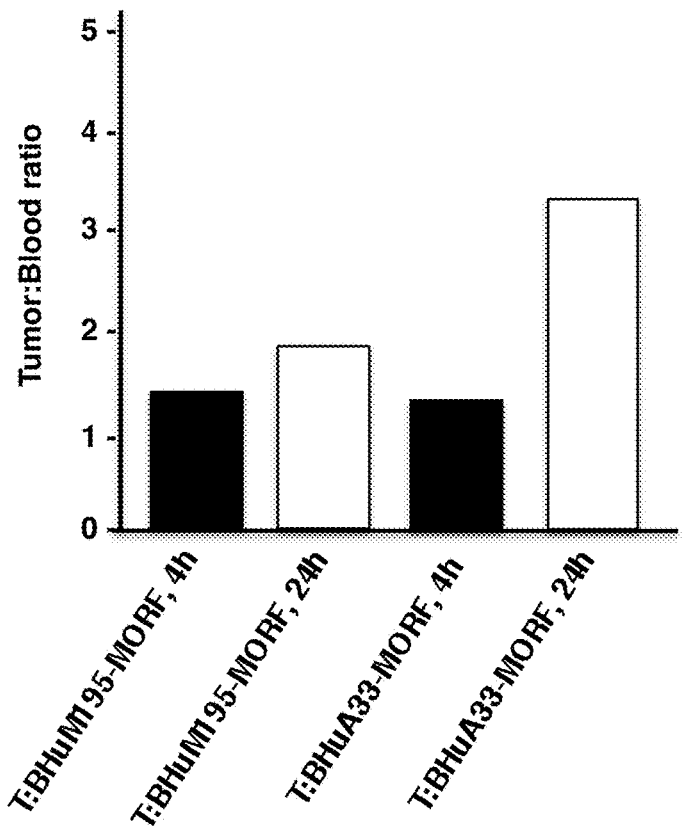
Figure 5D:
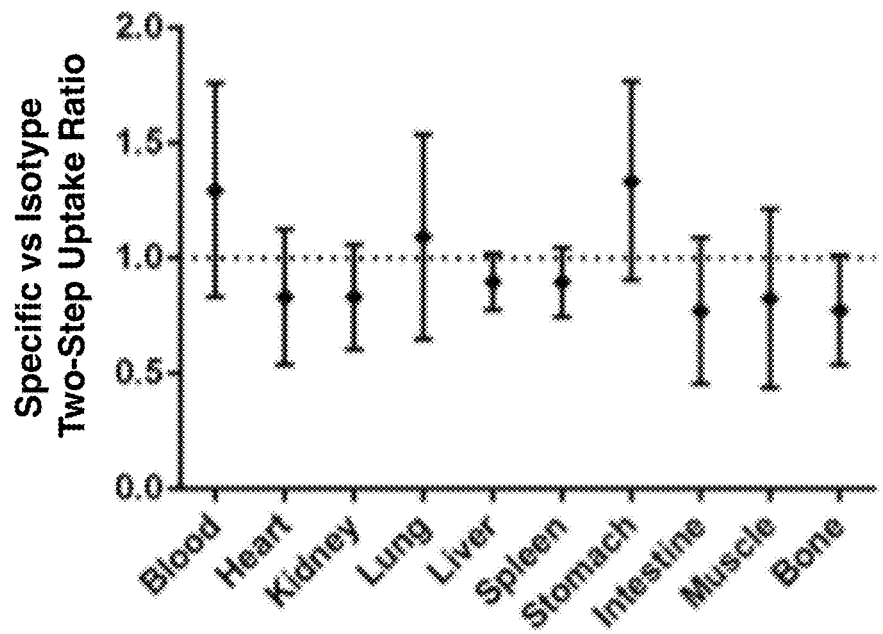

At 24 hours, SWNT-cMORF was better retained in the tumors of specifically targeted animals (FIG. 5C) and there was a modest, but significant increase in the tumor to blood ratio for the specifically targeted tumors (3.2) versus the isotype control (1.7). The tumor to blood ratio at this point was slightly improved as compared to what was obtained with directly labeled anti-A33 antibodies at 72 hours post-injection (3.2 vs 2.5). Unlike the tumor in FIG. 5C, no other measured tissues showed significant enhancement of specifically treated cells versus the isotype (FIG. 5D). The non-specific tumor accumulation in control antibody treated animals was attributed to the enhanced permeability and retention effect, which is known to passively accumulate carbon nanotubes in tumors (4). A panel of normal tissues was also harvested and demonstrated no significant difference between the two groups in any off-target sites, confirming the tumor-specificity of this increased accumulation. As with other covalently functionalized single-walled carbon nanotubes constructs (8), off-target accumulation in the kidneys, liver, and spleen also was observed.

EXAMPLE 7

SWNT-cMORF-DOTA as a Delivery Vehicle for $^{225}$Ac Mitigates Radioisotope Toxicity Having demonstrated the ability to target both solid and disseminated malignancies, it is demonstrated that the SWNT-cMORF constructs are effective carriers in a therapeutic model of human lymphoma using a xenografted SCID mouse model. A key property of any pretargeted vehicle for radio-immunotherapy is that the rapid clearance of the secondary agent offers improved therapeutic index due to reduced circulation time of a cytotoxic effector. A number of studies were performed previously demonstrating that covalently functionalized SWNT, even after addition of 18-mer oligonucleotides, have this rapid clearance (35). Similar biodistribution experiments performed with the constructs described herein demonstrated similar clearance properties. Biodistribution of SWNT-cMORF-($^{111}$In) in vivo was assessed both as total radiation and percent injected dose at 1, 4, 8, 12, and 24 hours after injection. As expected, the majority of the total injected dose (~77% ID) was excreted (largely in urine) by 24 hours and no organ other than the kidney had more than 0.2% of the injected dose per gram after 1 hour. The preponderance of remaining radiation localized to the kidneys (2.96% ID).

Rapid clearance of radiolabeled SWNT markedly reduces toxicity in mice when compared to similarly radiolabeled single-step monoclonal antibodies, free $^{225}$Ac or antibodies labeled with MRF directly. For monoclonal antibodies directly labeled with $^{225}$Ac, the maximum tolerated dose in mice is 400-500 nCi, usually 450 nCi, in a single injection, with acute toxicity and death resulting from marrow failure and longer-term renal toxicity from radioisotope daughters (36-37), whereas for $^{225}$Ac alone (FIG. 6A) this does is rapidly lethal.

Therefore, to demonstrate reduction in toxicity as compared to similarly labeled antibodies, the total amount of radioactivity administered ranged from 0 to 2700 nCi of $^{225}$Ac. Although dose-dependent weight loss was observed in mice receiving the radiolabeled SWNT-cMORF-$^{225}$Ac (DOTA) (FIG. 6A), all mice administered with SWNT-cMORF-$^{225}$Ac(DOTA) below 2250 nCi survived through the 140 day experiment. One of five mice and two of five mice died in the 2250 nCi and 2700 nCi dose level, respectively. Mice at dose levels of 1,350-2,700 nCi presented with limited dose-dependent toxicity, including reduced bone marrow and splenic cellularity and smaller glomeruli at 140 days. Mice at all doses with the exception of the free $^{225}$Ac group demonstrated normal grooming and feeding behaviors.

Figure 6B:
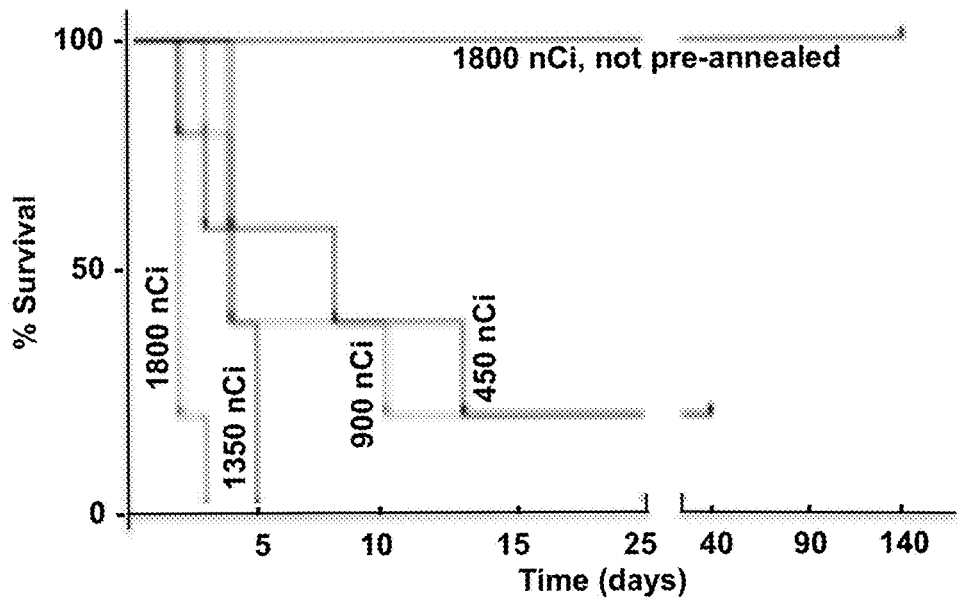

The pre-annealed single-step toxicity study conducted for comparison demonstrated that all dosing groups (450-1,800 nCi) reached a dose-dependent, terminal morbidity starting at 6 days post-injection, presumably resulting from the inability of the annealed structure to clear the kidneys (FIG. 6B). The maximum tolerated dose of the pre-annealed material (<450 nCi) was reached at a dose at least sixfold lower than when using the nanotube carrier (>2,700 nCi) and median survival was at least 10 times shorter (<2 weeks versus >20 weeks).

Figure 6C:
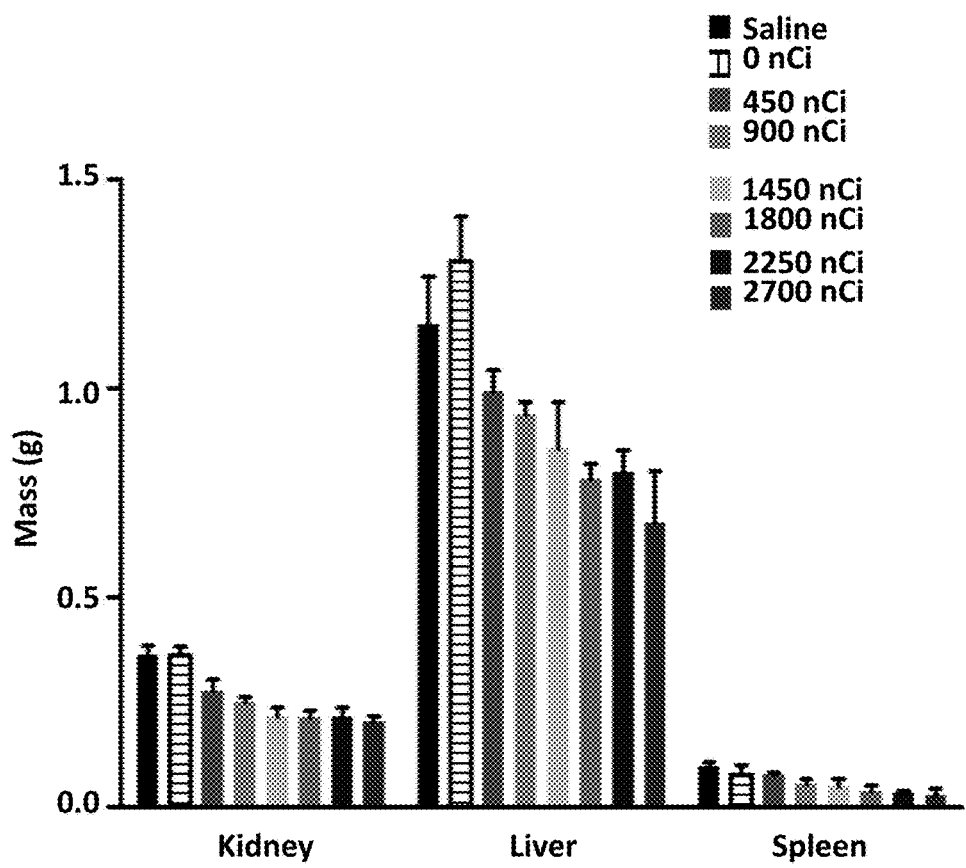

Modest dose-dependent weight loss was seen in the kidneys, liver, and spleen (the major sites of nonspecific uptake of the SWNT constructs) (FIG. 6C). As a comparison, 450 nCi of free actinium proved uniformly lethal at 4 days. Unlabeled nanotube-oligonucleotide conjugates were found to have no observable toxicity. Mice at dose levels of 0, 450, and 900 nCi showed no discernible organ damage upon microscopic histochemical evaluation, whereas at levels of 1350 to 2700 nCi organs showed limited dose-dependent toxicity including reduced bone marrow and splenic cellularity and smaller glomeruli at 140 days.

EXAMPLE 8

Therapy with SWNT-cMORF-($^{225}$Ac)DOTA

Figure 7A:
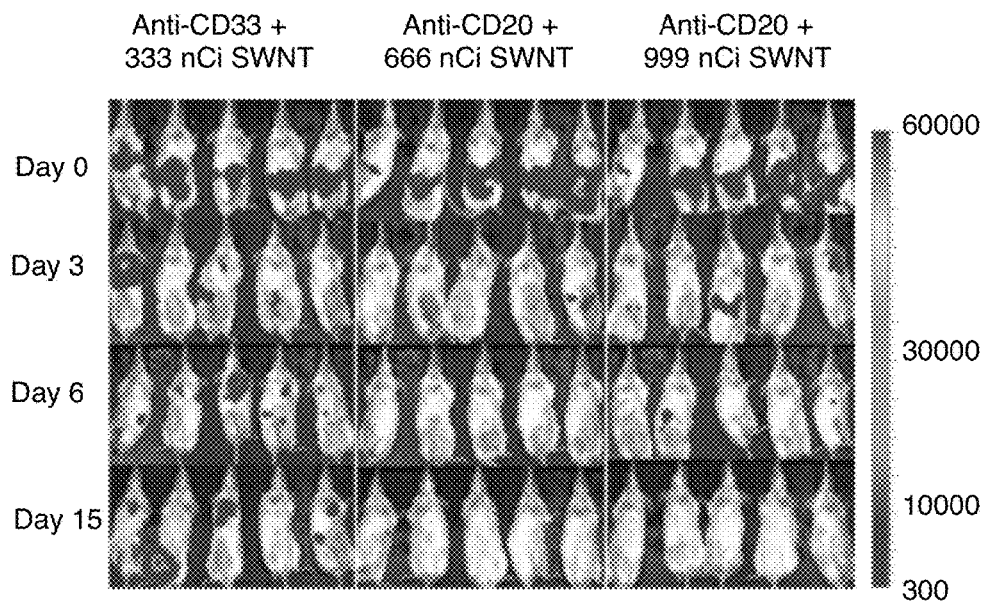
FIGS. 7A-7B illustrate the efficacy of SWNT-cMORF-($^{225}$Ac)DOTA (FIG. 7A) compared to controls (FIG. 7B) in multi-step therapy of disseminated lymphoma. Mice previously implanted with luciferase-transfected Daudi lymphoma cells that were injected with 5 mg/ml luciferin and were imaged after a 5 minute delay. Luminescence scale is the same for all images. The parameters are equivalent for all images, but, as a tradeoff, this leads to saturation that disallows quantification. Mice were treated with multistep therapy as previously noted and imaged at days 0, 3, 6, and 15 after treatment. Growth, rituximab therapy, isotype high-dose radiation and blocked two-step controls are provided.
Figure 7B:
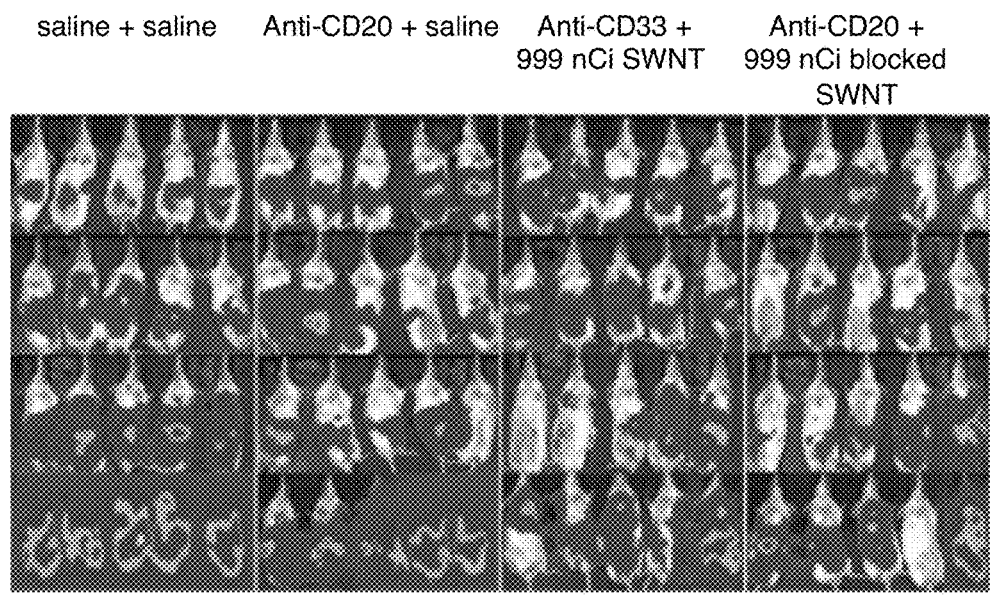

The high specific activity SWNT-cMORF-$^{225}$Ac is rapidly cleared and did not produce overt toxicity up to 1350 nCi. Mice were implanted with Daudi lymphoma cells in the peritoneal cavity followed by multistep therapy one week later, after tumor confirmation. The study included 10 groups of 5 mice each, consisting of 3 treatment groups and 7 control groups for SWNT-cMORF-$^{225}$Ac(DOTA) therapy of Daudi lymphoma as shown in Table 3 in Example 1. Tumor imaging studies demonstrated effective dose-dependent therapy in all 3 treatment groups (FIGS. 7A-7B).

There was complete elimination of tumor burden in treatment groups 8 and 9 (666 nCi SWNT-cMORF-$^{225}$Ac (DOTA) and 999 nCi SWNT-cMORF-$^{225}$Ac(DOTA). Mice in the saline control, and cold SWNT control showed rapid progression of tumor burden. Mice treated with anti-CD20-MORF alone showed a brief reduction in tumor load that was attributed to a transient response to the unlabeled anti-CD20 antibody, which is known to be therapeutic (Rituximab). Mice treated with the isotype control anti-CD33-MORF followed by SWNT-cMORF-$^{225}$Ac(DOTA) at several dose levels showed transient responses, attributable to non-specific irradiation from $^{225}$Ac. Finally, to demonstrate that the therapeutic effect was due to self-assembly and not simply additive effects of each component of the therapy, a dual control of anti-CD20-MORF followed by SWNT-cMORF-$^{225}$Ac(DOTA) that had been mixed with excess free MORF to block hybridization was included. In this group, four of five mice had marked tumor progression, while one mouse had a therapeutic response attributed to the additive effects of ADCC and non-specific radiation.

The following references are cited herein:
1. Scheinberg et al. Nat Rev Clin Oncol, 7:266-276 (2010).
2. Davis et al. Nature Reviews Drug Discovery, 7:771-782 (2008).
3. Kostarelos et al. Nature Nanotech, 4:627-633 (2009).
4. Liu et al. Cancer Res, 68:6652-6660 (2008).
5. Liu et al. Nat Nano, 2:47-52 (2007).
6. Villa et al. ACS Nano, null-null (2011).
7. Villa et al. Nano Lett, 8:4221-4228 (2008).
8. McDevitt et al. PLoS ONE, 2:e907 (2007).
9. McDevitt et al. J Nucl Med, 48:1180-1189 (2007).
10. Ruggiero et al. International Journal of Nanomedicine, 5:783-802 (2010).
11. Singh et al. Proc Natl Acad Sci USA, 103:3357-3362 (2006).

12. Liu et al. Proc Natl Acad Sci USA, (2008).
13. Mutlu et al. Nano Lett., 10(5):1664-1670a (2010).
14. Ruggiero et al. Proceedings of the National Academy of Sciences of the United States of America 107:12369-12374 (2010).
15. Lacerda et al. Small, 4:1130-1132 (2008).
16. Kostarelos, K. Nat Mater, 9:793-795 (2010).
17. Goldenberg et al. Journal of Clinical Oncology (2006).
18. Green et al. Cancer Res, 13:5598s-5603s (2007).
19. Sharkey et al. Leukemia, 19:1064-1069 (2005).
20. Liu et al. Clin Cancer Res, 12:4958-4964 (2006).
21. Rossin et al. Angew Chem Int Ed Engl, 49:3375-3378 (2010).
22. Perrault et al. PNAS 107(25):11194 (2010).
23. Park et al. PNAS 107(3):981 (2010).
24. Alvarez-Diez et al. Nuclear Medicine and Biology 23(4):459-466 (1996).
25. Liu et al. J Nucl Med (2004).
26. He et al. Molecular Pharmaceutics (2010).
27. Georgakilas et al. J Am Chem Soc, 124:760-761 (2002).
28. Georgakilas et al. Amino Chem Commun (Camb), 3050-3051 (2002).
29. He et al. Bioconjug Chem, 18:983-988 (2007).
30. Kaiser et al. Anal Biochem, 34:595-598 (1970).
31. Liu et al. Eur J Nucl Med Mol Imaging, 34:237-246 (2007).
32. McDevitt et al. Science, 294:1537-1540 (2001).
33. le Maire et al. Anal Biochem, 177V50-56 (1989).
34. Ackerman et al. Cancer Immunol Immunother, 57:1017-1027 (2008).
35. Villa et al. Nano Lett 8:4221-4228 (2008).
36. Miederer et al. Adv Drug Deliv Rev 60:1371-1382 (2008).
37. Song et al. Cancer Research 69:8941-8948 (2009).

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for delivering a therapeutic radionuclide in situ to a cancer cell of interest in a subject, comprising:

contacting the cancer cell with a first component comprising a morpholino oligonucleotide consisting of SEQ ID NO: 1 linked to an antibody selective for the cancer cell;

contacting the first component with a second component comprising a soluble single wall nanotube construct having:

a plurality of morpholino oligonucleotides each consisting of SEQ ID NO: 2 complementary to the morpholino oligonucleotide sequence consisting of SEQ ID NO: 1 in the first component; and a plurality of the therapeutic radionuclide each independently linked to the single wall nanotube via a bifunctional chelator; said first component hybridizing to the second component upon contact therewith to form a self-assembled soluble single wall nanotube complex at the cancer cell, wherein the self-assembled soluble single wall nanotube complex is capped and internalized, thereby delivering in situ the therapeutic radionuclide to the cancer cell of interest in the subject.

2. The method of claim 1, wherein the antibody is a monoclonal antibody.

3. The method of claim 2, wherein the monoclonal antibody is an anti-CD20, anti-CD33, or anti-A33 monoclonal antibody or a single chain variable fragment (scFv) or fragment antigen-binding (Fab) fragment thereof.

4. The method of claim 1, where the cancer cell is a lymphoma cancer cell, a leukemia cancer cell or a colon cancer cell.

5. The method of claim 1, wherein the bifunctional chelator is (4-isothiocyanatobenzyl)-1,4,7,10-tetraazacyclododecane-1,4,7,10-tetraacetic acid (DOTA) or diethylenetriaminepentaacetic acid (DTPA).

6. The method of claim 1, wherein the therapeutic radionuclide is actinium-225, astatine-211, technetium-99, lutetium-177, gallium-68, holmium-166, bismuth-212, bismuth-213, yttrium-90, copper-67, samarium-117, samarium-153, iodine-123, or iodine-131.

7. The method of claim 1, further comprising treating a cancer comprising the cancer cell with the therapeutic radionuclide after in situ delivery thereof to the cancer cell in the subject.

8. The method of claim 7, wherein the cancer is a lymphoma, a leukemia or a colon cancer.

* * * * *